(12) United States Patent
Xu et al.

(10) Patent No.: US 11,834,707 B2
(45) Date of Patent: Dec. 5, 2023

(54) NUCLEIC ACID AMPLIFICATION BLOCKER FOR DETECTING LOW-ABUNDANCE MUTATION SEQUENCE AND APPLICATION THEREOF

(71) Applicant: SHANGHAI MAG-GENE NANOTECH CO., LTD., Shanghai (CN)

(72) Inventors: Hong Xu, Shanghai (CN); Hao Yang, Shanghai (CN); Gaolian Xu, Shanghai (CN); Hongchen Gu, Shanghai (CN)

(73) Assignee: SHANGHAI MAG-GENE NANOTECH CO., LTD., Shanghai (CN)

( * ) Notice: Subject to any disclaimer, the term of this patent is extended or adjusted under 35 U.S.C. 154(b) by 0 days.

(21) Appl. No.: 17/312,398

(22) PCT Filed: Dec. 11, 2019

(86) PCT No.: PCT/CN2019/124574
§ 371 (c)(1),
(2) Date: Jun. 10, 2021

(87) PCT Pub. No.: WO2020/119721
PCT Pub. Date: Jun. 18, 2020

(65) Prior Publication Data
US 2022/0025452 A1    Jan. 27, 2022

(30) Foreign Application Priority Data

Dec. 12, 2018  (CN) .......................... 201811518798.3

(51) Int. Cl.
*C12Q 1/6858*  (2018.01)
*C12Q 1/6853*  (2018.01)
*C12Q 1/6876*  (2018.01)

(52) U.S. Cl.
CPC ......... *C12Q 1/6858* (2013.01); *C12Q 1/6853* (2013.01); *C12Q 1/6876* (2013.01); *C12Q 2525/113* (2013.01); *C12Q 2525/186* (2013.01); *C12Q 2527/107* (2013.01); *C12Q 2537/163* (2013.01)

(58) Field of Classification Search
CPC .. C12Q 1/6858; C12Q 1/6853; C12Q 1/6876; C12Q 2525/113; C12Q 2525/186; C12Q 2527/107; C12Q 2537/163; C12Q 2525/117
See application file for complete search history.

(56) References Cited

U.S. PATENT DOCUMENTS

2006/0068433 A1* 3/2006 Godfrey ............... C12Q 1/6886
435/6.1

FOREIGN PATENT DOCUMENTS

| CN | 101608240 B | 6/2011 |
|---|---|---|
| CN | 102747157 A | 10/2012 |
| CN | 103215361 A | 7/2013 |
| CN | 103255201 A | 8/2013 |
| CN | 105164280 A | 12/2015 |
| CN | 105358710 A | 2/2016 |
| CN | 104762408 B | 6/2017 |
| CN | 107034277 A | 8/2017 |
| CN | 109652410 A | 4/2019 |

OTHER PUBLICATIONS

Vestheim et al. Blocking primers to enhance PCR amplification of rare sequences in mixed samples—a case study on prey DNA in Antarctic krill stomachs. Frontiers in Zoology 2008; 5: 12. (Year: 2008).*
Owczarzy et al. Predicting Stability of DNA Duplexes in Solutions Containing Magnesium and Monovalent Cations. Biochemistry 2008; 47: 5336-5353. (Year: 2008).*
Suzuki et al. Quantitative Analysis of Small-Subunit rRNA Genes in Mixed Microbial Populations via 5'-Nuclease Assays. Applied and Environmental Microbiology 2000; 66: 4605-4614. (Year: 2000).*
Wang et al. Allele-Specific, Non-Extendable Primer Blocker PCR (AS-NEPB-PCR) for DNA Mutation Detection in Cancer. The Journal of Molecular Diagnostics 2013; 15: 62-69. (Year: 2013).*
Efrati et al. LNA-based PCR clamping enrichment assay for the identification of KRAS mutations. Cancer Biomarkers 2010; 8: 89-94 (Year: 2010).*

(Continued)

*Primary Examiner* — Angela M. Bertagna
(74) *Attorney, Agent, or Firm* — Bayramoglu Law Offices LLC

(57) ABSTRACT

A nucleic acid amplification blocker for detecting a low-abundance mutation sequence and an application thereof in detecting a low-abundance mutation sequence are provided. The nucleic acid amplification blocker is an oligonucleotide modified by locked nucleic acid (LNA), and the matching region of the nucleic acid amplification blocker is located between amplified sequences. The nucleic acid amplification blocker is completely complementary to wild-type gene sequence, and contains at least one mismatch with mutant sequence. The nucleic acid amplification blocker has a great difference in affinity with mutant nucleic acid sequence/wild-type nucleic acid sequence, so as to achieve the purpose of highly selective amplification/enrichment of mutant sequence in samples. The nucleic acid amplification blocker has more significant detection effect on deletion mutation and insertion mutation.

12 Claims, 8 Drawing Sheets
Specification includes a Sequence Listing.

(56) References Cited

OTHER PUBLICATIONS

Yoon et al. KRAS Codon 12 and 13 Mutations in Relation to Disease-Free Survival in BRAF-Wild-Type Stage III Colon Cancers from an Adjuvant Chemotherapy Trial (N0147 Alliance). Clinical Cancer Research 2014; 20: 3033-304 (Year: 2014).*

Morlan et al. Mutation Detection by Real-Time PCR: A Simple, Robust and Highly Selective Method. PLoS One 2009; 4: e4584 (Year: 2009).*

Mi Jung Kwon, et al., Frequency of KRAS, BRAF, and PIK3CA mutations in advanced colorectal cancers: Comparison of peptide nucleic acid-mediated PCR clamping and direct sequencing in formalin-fixed, paraffin-embedded tissue, Pathology—Research and Practice, 2011, pp. 762-768, 207.

J. Sambrook, et al., Molecular Cloning, A Laboratory Manual Second Edition, 1989, pp. 1.53-1.86.

Patrick L Dominguez, et al., Wild-type blocking polymerase chain reaction for detection of single nucleotide minority mutations from clinical specimens, Oncogene, 2005, pp. 6830-6834, 24.

Jia Peng, et al., Wild-type blocking pcr coupled with internal competitive amplified fragment improved the detection of rare mutation of KRAS, Molecular Medicine Reports, 2017, pp. 2726-2732, 16.

Toshitsugu Fujita, et al. A refined two-step oligoribonucleotide interference-PCR method for precise discrimination of nucleotide differences, Scientific Reports, 2018, pp. 1-16, 8:17195.

Lone Hummelshoj, et al., Locked nucleic acid inhibits amplification of contaminating DNA in real-time PCR, BioTechniques, 2005, pp. 605-610, vol. 38, No. 4.

Xiyuan Sun, et al., Detection of tumor mutations in the presence of excess amounts of normal DNA, Technical Report, 2002, pp. 186-189.

Liang Cui, Design, Synthesis and Investigation of Locked Nucleic Acid, Molecular Beacons, 2009, 57 pages.

* cited by examiner

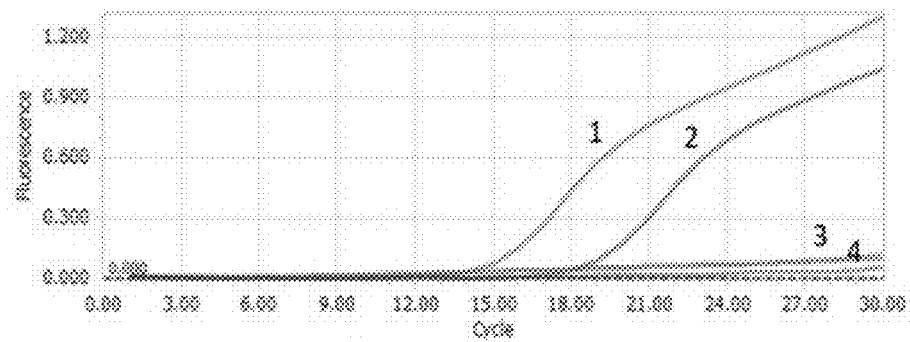
FIG. 4D
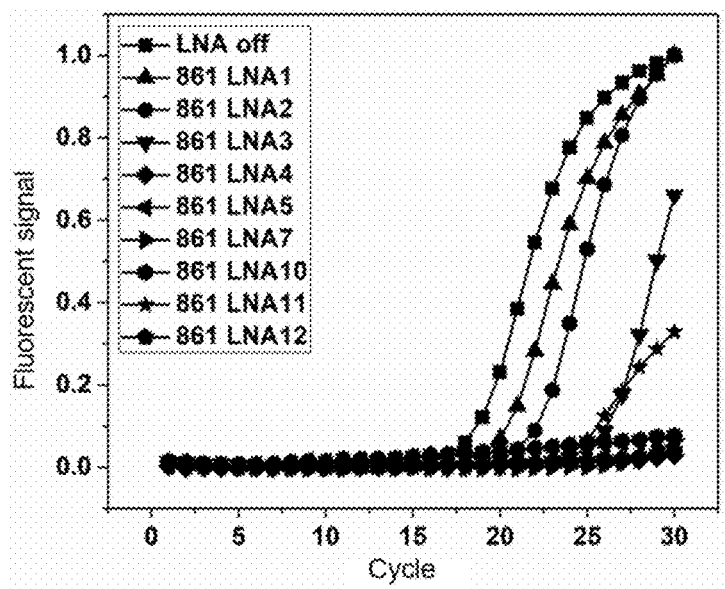
FIG. 5
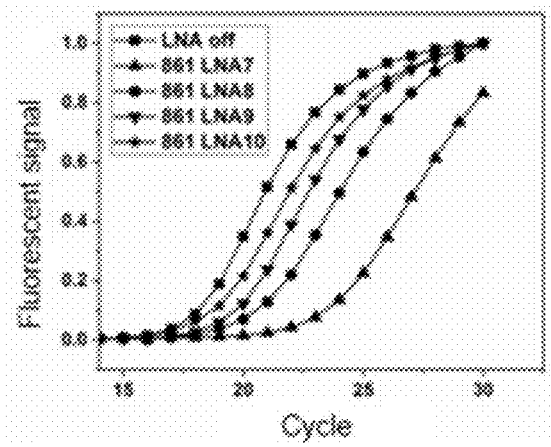  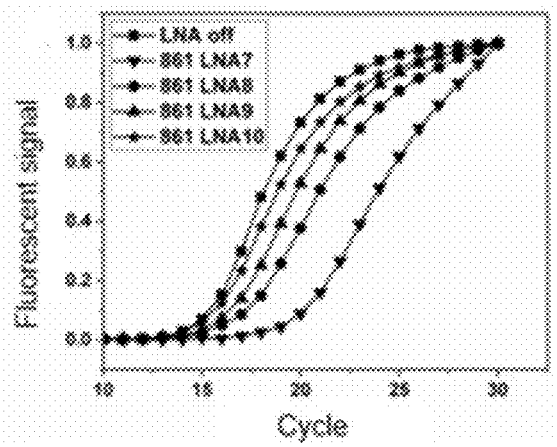
FIG. 6A  FIG. 6B

NUCLEIC ACID AMPLIFICATION BLOCKER FOR DETECTING LOW-ABUNDANCE MUTATION SEQUENCE AND APPLICATION THEREOF

CROSS REFERENCE TO THE RELATED APPLICATIONS

This application is the national phase entry of International Application No. PCT/CN2019/124574, filed on Dec. 11, 2019, which is based upon and claims priority to Chinese Patent Application No. 201811518798.3, filed on Dec. 12, 2018, the entire contents of which are incorporated herein by reference.

SEQUENCE LISTING

The present application contains a Sequence Listing which has been submitted in ASCII format via EFS-Web and is hereby incorporated by reference in its entirety. Said ASCII copy is named GBSHZW001-PKG-Sequence-Listing.txt, created 7/27/2021, and 13,234 bytes in size.

TECHNICAL FIELD

The present invention relates to the field of detection of mutant genes, in particular to a design principle and application of a nucleic acid amplification blocker for a low-abundance mutant sequence.

BACKGROUND

Gene mutations are changes in gene structure caused by addition, deletion or change of base pairs in DNA molecules. Gene mutations are related to many disease symptoms, such as tissues and a small amount of circulating tumor DNA in the peripheral blood of tumor patients, and the initial emergence of bacterial or viral resistance. Therefore, the mutant genes can be used as landmark for disease detection, prognosis prediction and medication guidance. Whereas the nucleic acid-based amplification is the most common method for mutation gene detection.

Nucleic acid amplification is the basic step in most nucleic acid assays. Accurate detection of nucleic acid generally refers to the ability for amplifying the specific target nucleic acids in the presence of excessive non-target nucleic acids, and the non-target nucleic acid has a sequence similar to that of the target nucleic acid. In some cases, the difference between the non-target nucleic acid and the target nucleic acid is as little as one nucleotide (or one nucleotide base pair). For example, in tumor detection and personalized treatment, it is necessary to detect traces of tumor-related mutant alleles in excessive wild sequences sensitively and reliably, which is essential to early diagnosis or definite diagnosis, treatment decisions, disease monitoring and prognosis prediction. However, a highly sensitive and specific detection of mutant sequences in the background of a large number of wild non-target alleles remains a great challenge.

At present, methods to detect a small number of gene mutations mainly include sequencing-based methods, traditional fluorescence quantitative polymerase chain reaction (qPCR) and high resolution melting curve. These methods still fall short of sensitivity and throughput when being used for detecting mutant genes.

Sanger sequencing method: First, corresponding primers were designed for the mutation sites, then target gene products were obtained through PCR amplification, and finally, the PCR products were sequenced and the sequencing results were analyzed. Such sequencing method has low sensitivity and can only be used to detect gene mutations that account for more than 20%. Therefore, this method is not suitable for the analysis of a large number of clinical samples.

Denaturing high performance liquid chromatography: This method can be applied to separate heteroduplexes incurring mismatch from completely matching homoduplexes based on different denaturation characteristics of the two. Since the heteroduplexes incur mismatch at mutation sites, which is prone to forming special structures that weakly bind to solid phases, as a result, the heteroduplexes are eluted prior to the homoduplexes. Different elution peaks indicate whether there is gene mutation. However, this method relies on expensive instruments and requires high proficiency of operators. Meanwhile, a sample to be detected needs to be highly pure and over 0.01 ng, thus the method is insufficiently sensitive.

High resolution melting (application No: CN104762408B): Saturated dyes are bound to PCR amplification products, and the change in melting curve of the PCR amplification products is monitored based on the physical properties of nucleic acid to analyze gene mutations. The detection sensitivity is about 5%. Whereas, the definite sites of the detected mutations cannot be specified for the positive results, which eventually need to be confirmed by sequencing methods.

Amplification refractory mutation system (ARMS) (Application No: CN101608240B/CN102747157A): based on the principle that the 3-terminal base of a PCR primer must be complementary to the template for an effective amplification, specific PCR primers are designed for mutation sites to achieve mutation detection. This method is simple and time-saving, but requires identification of mutation types in advance. Furthermore, false positive results are likely to occur when a high concentration of wild templates is used. Moreover, the detection sensitivity of this method merely reaches 1%.

TaqMan mismatch amplification mutation: in this method, mismatch sequences are introduced to use as probes and an amplification signal will be detected only in the presence of a mutated sequence. This method, however, easily produces false positive results when wild templates are used at an excessively high concentration. While once obtaining negative results, the identification of mutations requires additional operations. Accordingly, this method is not adequate enough.

In order to overcome the inherent shortcomings of existing techniques and improve the sensitivity and reliability of nucleic acid assays, the majority of current amplification methods use peptide nucleic acid (PNA)-mediated nucleic acid amplification blockers (CN 105164280 A, Lee et al. 2011, Sun et al. 2002). The PNA-mediated nucleic acid amplification blockers, however, are expensive, and may cause certain inhibitory effects on the mutant template amplification while normally inhibiting wild templates, which leads to the reduction of detection sensitivity. Furthermore, PNA has some problems such as extremely high cost, long synthesis cycle, single design method and poor solubility.

Therefore, technicians in the field have focused on developing a method for detecting low-abundance mutation sequences, which is highly sensitive and easily operative.

SUMMARY

In view of this, the present invention provides a nucleic acid amplification blocker that can be used to detect low-abundance mutated DNA sequences in the presence of a large number of wild sequences. The nucleic acid amplification blocker involves a chemical modification of an oligonucleotide so that the chemically modified oligonucleotide contains a specific locked nucleic acid (LNA) base.

The first aspect of the present invention provides a blocker. In a specific embodiment, the matching region of the blocker is located in the amplification region amplified between a first primer and a second primer, and the 3' end is modified to inhibit a primer extension reaction. The blocker is completely complementary to a second allele variant and has at least one base mismatch with a first allele variant, and the blocker includes LNA modifications. The melting temperature (Tm) value of the blocker is at least 7.5° C. higher than that of the first primer. Specifically, the content of the first allele variant is lower or far lower than that of the second allele variant, and the blocker can compete with the first primer to bind to the second allele variant. The Tm values of the blocker and the first primer are obtained by calculation.

Optionally, the 3' end of the blocker is modified with a non-hydroxyl group to inhibit the primer extension reaction. Optionally, the non-hydroxyl group modification includes, but is not limited to, phosphorylation, amination, deoxygenation, halogenation, C3 Spacer modification, and C6 Spacer modification.

Optionally, the difference obtained from the Tm value of the blocker minus the Tm value of the first primer is between 7.5° C. and 12° C.

Further, Tm value of the blocker and the difference of Tm value between blocker and first primer are adjusted by changing the number of LNA modifications, LNA modification site and the length of the blocker. Moreover, the difference obtained from the Tm value of the blocker binding to the second allele variant minus the Tm value of the blocker binding to the first allele variant can also be adjusted by changing the number of LNA modifications, LNA modification site and the length of the blocker. The inhibitory effect of the blocker on the amplification of the first allele variant decreases as the difference increases.

Further, the blocker includes the 5' end region, the central region, and the 3' end region. Specifically, the base of the blocker that is mismatched with the first allele variant is located in the central region and has LNA modification. Optionally, the central region is a segment having a length approximately one third of the length of the blocker and located in the middle of the blocker.

Further, the 3'-terminal base and 5'-terminal base of the blocker are not modified with LNA.

Further, the number of LNA modifications in the blocker is greater than or equal to 4; and/or the length of the blocker is greater than or equal to 14 bases. Optionally, the number of LNA modifications in the blocker is greater than or equal to 4 and less than or equal to 6. Optionally, the length of the blocker is greater than or equal to 14 bases and less than or equal to 16 bases.

Further, the first allele variant is a mutant allele, and the second allele variant is a wild-type allele. The mutation of the first allele is point mutation, insertion mutation or deletion mutation. When calculating the Tm value of the blocker and the Tm value of the first primer, the concentrations of primers, magnesium ions, sodium ions and deoxynucleotide (dNTP) in the reaction system of the amplification reaction should be considered.

Further, the blocker is shown in SEQ ID NO: 4, SEQ ID NO: 6, SEQ ID NO: 7, SEQ ID NO: 18, SEQ ID NO: 19, or SEQ ID NO: 20.

In another specific implementation way, a nucleic acid amplification blocker for detecting a low-abundance mutation sequence is provided. The nucleic acid amplification blocker is an oligonucleotide modified by locked nucleic acid (LNA), and the matching region of the nucleic acid amplification blocker is located between the amplified sequences, which is completely matched with the wild-type gene sequence, and contains at least one mismatch with the mutant sequence.

LNA, as a nucleotide chemical modification, has many advantages such as high affinity, flexible base modification site, good thermal stability, low price, etc., and can be synthesized by a solid phase method just like ordinary DNA primers. In a specific embodiment of the present invention, an LNA-modified nucleic acid amplification blocker will cover the target mutation site and require being fully complementary to the wild-type sequence. Therefore, the nucleic acid amplification blocker can effectively bind to the wild-type sequence to block the nucleic acid amplification reaction under suitable reaction conditions. Meanwhile, its affinity with the mutated sequence is significantly reduced due to the existence of mismatched bases, achieving the purpose of highly selective amplification, so its detection effect for the deletion mutation and the insertion mutation is more significant.

Further, the number of LNA modifications in the nucleic acid amplification blocker ranges from 1 to 8, and the length thereof ranges from 12 to 30 nucleotides. Preferably, the number of LNA modifications in the nucleic acid amplification blocker is 3-5, and the length thereof is 14-18 nucleotides. Moreover, the designed LNA sequence can contain at most 2 LNA-modified bases in the secondary structure formed by itself.

The annealing temperature of the nucleic acid amplification blocker is 6-15° C. higher than that of the amplification primer.

Further, the nucleic acid amplification blocker is synthesized by the solid phase method.

Further, the 3' terminal of the nucleic acid amplification blocker is modified with a non-hydroxyl group.

Further, the non-hydroxyl group modification includes, but is not limited to, phosphorylation, amination, deoxygenation, halogenation, C3 Spacer modification, and C6 Spacer modification.

Further, the mutation sequence is point mutation, insertion mutation and deletion mutation.

The second aspect of the present invention provides a composition, and in a specific embodiment, the composition includes:

1) the first primer and the second primer configured to specifically amplify the target nucleic acid sequence of the first allele variant; wherein the 3'-terminal base of the first primer is complementary to the mutation site of the first allele variant, and the Tm value of the first primer is greater than or equal to 60° C.; and 3) the blocker as mentioned above.

In some embodiments, the composition also includes 3) a detection probe, wherein an amplicon of a mutated target nucleic acid sequence is detected based on the change in detectable properties of the detection probe.

In some embodiments, a detection probe is needed to provide a detection signal as a basis for a quantitative PCR (qPCR)-based detection; in some embodiments, a detection probe is not required in a detection based on electrophoresis or chip hybridization.

The third aspect of the present invention provides a method for designing a blocker. In a specific embodiment, the blocker is completely complementary to the second allele variant and contains at least one base mismatch with the first allele variant, and the base that forms a mismatch with the first allele variant is located in the central region of the blocker.

By adjusting the number of LNA modifications, the LNA modification site and/or the length of the blocker, the Tm value of the blocker is at least 7.5° C. higher than that of the first primer. In addition, changing the number of LNA modifications, the LNA modification site and the length of the blocker can also adjust the difference obtained from the Tm value of the blocker binding to the second allele variant minus the Tm value of the blocker binding to the first allele variant. The inhibitory effect of the blocker on the amplification of the first allele variant decreases as the difference increases. The Tm value of the blocker and the Tm value of the first primer are obtained by calculation.

Optionally, the difference obtained from the Tm value of the blocker minus the Tm value of the first primer is between 7.5° C. and 12° C.

Further, adjusting the number of LNA modifications, the LNA modification site and the length of the blocker specifically includes: adding at least one LNA modification in each adjustment starting with the initial number of 4 LNA modifications, adding at least one base in length in each adjustment starting with the initial length of 14 bases; and performing the LNA modification on mutant site of the blocker while not performing the LNA modifications on the 3'-terminal base nor the 5'-terminal base of the blocker.

Optionally, the number of LNA modifications is 4 to 6. The length of the blocker is 14 to 16 bases.

Optionally, the method of designing the blocker includes the following steps:

S100, determining an initial sequence of the blocker based on the initial length of 14 bases;

S200, performing an LNA modification starting with an initial number of 4 LNA modifications; wherein the LNA modification is performed on a base of the blocker mismatched with the first allele variant, and the LNA modification is not performed on the 3'-terminal base nor the 5'-terminal base of the blocker;

S300, checking whether the blocker has a hairpin structure or a self-folding structure (especially a hairpin structure with LNA-LNA matching); if not, proceeding to S400; if yes, returning to S100;

S400, checking the difference obtained from the Tm value of the blocker minus the Tm value of the first primer; if the difference is less than 7.5° C., the number of LNA modifications is less than 6, and the length of the blocker is less than 16 bases, entering S500; if the difference is less than 7.5° C., the number of LNA modifications is 6, and the length of the blocker is equal to 16 bases, then entering S100; if the difference is greater than or equal to 7.5° C., determining it as a suitable blocker; and S500, increasing the number of LNA modifications of the blocker by one, and/or increasing the length of the blocker by one base; then entering S300.

The fourth aspect of the present invention provides a method for detecting an allelic mutation. In a specific embodiment, the method includes:

a) mixing i) a nucleic acid sample, ii) the first primer and the second primer, and iii) the nucleic acid amplification blocker to form a reaction mixture; wherein the first primer and the second primer are used to specifically amplify the target nucleic acid sequence of the first allele variant; the 3'-terminal base of the first primer is complementary to the mutation site of the first allele variant, and the Tm value of the first primer is greater than or equal to 60° C.; a matching region of the blocker is located in the amplification region of the first primer and the second primer, and the 3' end can inhibit the primer extension reaction; the blocker is completely complementary to the second allele variant, and contains at least one base mismatch with the first allele variant, and the blocker includes LNA modification; and the Tm value of the blocker is at least 7.5° C. higher than that of the first primer;

b) conducting an amplification reaction, and forming the target nucleic acid sequence amplicon of the first allele variant through the amplification of the first primer and the second primer; and c) performing a detection.

Optionally, the detection is performed based on electrophoresis or chip hybridization without detection probe.

Optionally, step a) of the method further includes iv) a detection probe; step c) of the method is to performing the detection based on a change in detectable properties of the detection probe to detect the target nucleic acid sequence amplicon, so as to detect the first allele variant in the nucleic acid sample.

Further, the method provides the possibility to detect the first allele variants having the number ranging from 10 to 100 in the presence of 10,000 second allele variants.

Further, the concentration of the blocker is 5-20 times the concentration of the first primer and the second primer. Optionally, the concentration of the blocker is 10 to 20 times that of the first primer and the second primer. The second allele variant having a high concentration is inhibited by the difference between the Tm value of the first primer and the Tm value of the blocker and the difference between the concentration of the first primer and the concentration of the blocker. LNA modification principle is used to minimize the impact on the amplification of low-abundance mutant genes.

The fifth aspect of the present invention provides a kit containing the blocker as mentioned above, a blocker designed by the method for designing blocker as mentioned above, or the composition as mentioned above.

The sixth aspect of the present invention also provides an application of the blocker in the detection of allelic mutation. In a specific embodiment, the blocker as mentioned above or a blocker designed by the method of designing blocker as mentioned above is added to an amplification reaction for detecting a mutant sequence.

Optionally, the amplification reaction includes, but is not limited to, isothermal amplification technology, and polymerase chain reaction (PCR). The isothermal amplification technology includes, but is not limited to, loop-mediated isothermal amplification technology (LAMP), nucleic acid sequence-based amplification (NASBA), rolling circle amplification (RCA), isothermal helicase-dependent amplification (HDA), strand displacement amplification (SDA), and nicking enzyme mediated amplification (NEMA). The polymerase chain reaction (PCR) includes, but is not limited to, real-time fluorescent quantitative PCR.

In another specific embodiment, an application of the nucleic acid amplification blocker in detecting low-abundance mutant sequences is provided. LNA-modified nucleic acid amplification blocker is added to the amplification reaction for detecting a mutation sequence.

Further, the concentration of the LNA-modified nucleic acid amplification blocker in the amplification reaction system is 0.01-1 μM, preferably 0.05-0.3 μM, and more preferably 0.1-0.2 μM.

Further, the amplification reaction includes, but is not limited to, isothermal amplification technology, and polymerase chain reaction (PCR). The isothermal amplification technology includes, but is not limited to, loop-mediated isothermal amplification (LAMP), nucleic acid sequence-based amplification (NASBA), rolling circle amplification (RCA), isothermal helicase-dependent amplification (HDA), chain displacement amplification (SDA), and nicking enzyme mediated amplification (NEMA).

Further, the amplification reaction described is real-time fluorescent quantitative PCR Compared with the prior art, the present invention has the following advantages:

The present invention provides an LNA-modified nucleic acid amplification blocker. During a nucleic acid amplification, the LNA-modified nucleic acid amplification blocker shows a strong affinity with wild-type sequences, so it will preferentially bind to the wild-type sequences specifically, which can effectively prevent amplified primers from binding to the wild-type nucleic acids, so as to achieve the purpose of preventing primer extension. At the same time, due to the difference between the LNA-modified nucleic acid amplification blocker and mutated nucleic acid sequences, the binding affinity between the two will be seriously reduced, thus the LNA-modified nucleic acid amplification blocker is unable to bind to the mutated nucleic acid sequence specifically and effectively, thereby failing to prevent the amplification and extension process of the primers. Therefore, a highly selective amplification/collecting mutant sequences of sample is realized based on the huge difference between affinity of the LNA-modified nucleic acid amplification blocker with mutant nucleic acid sequences and affinity of the LNA-modified nucleic acid amplification blocker with wild-type nucleic acid sequences, and at the same time, the detection effect for deletion mutations and insertion mutations is more significant. This kind of nucleic acid blocker has many advantages such as high affinity, flexible base modification site, good thermal stability, low price, etc., and can be synthesized by a solid phase method just like common DNA primers.

The blocker in the specific embodiment of the present invention is controllable in the number of LNA modifications, the LNA modification site and the length of the blocker under the premise that the blocker can inhibit the amplification of wild-type genes but does not inhibit the amplification of mutant genes. For example, in some embodiments, the number of LNA modifications is controlled at 4-6, and the length of the blocker is controlled within 14-16 bases, thus controlling the preparation cost of the blocker itself.

The method of designing nucleic acid amplification blocker in the specific embodiment of the present invention can quickly obtain a highly specific blocker with the minimum number of LNA modifications and the shortest length of the blocker. The difference (ΔTm) between the Tm value (obtained by calculation) of the blocker and the Tm value (obtained by calculation) of the first primer (pre-primer) is controlled being greater than or equal to 7.5° C., thus inhibiting the high-abundance wild-type genome. The difference (ΔTm') between the Tm value of the blocker binding to wild-type genes and the Tm value of the blocker binding to mutant genes is significant, thus not affect the amplification of the mutant genes.

Traditional LNA-modified blockers do not have a clear design scheme, and there is also no definite criterion for the number of LNA modifications, the LNA modification site and the length of the blockers, so the synthesized LNA-modified blockers are usually unsatisfactory. While in the design method of nucleic acid amplification blocker according to the specific embodiment of the present invention, starting with the length of 14 bases and 4 LNA modifications, the length of the blocker and the number of LNA modifications are adjusted to satisfy the requirement of melting temperature. The optimal LNA-modified blocker can be determined based on the Tm value calculated after a couple of designs and simulations, without the need of performing experiments or merely requiring few experiments. Therefore, the optimal amplification effect (there is no inhibition on the amplification of mutant genes while the amplification of wild-type genes is inhibited) can be ensured while minimizing the experimental cost. The design scheme is highly optimized for general use, almost suitable for all single nucleotide polymorphism (SNP) detection models.

In order to fully understand the purposes, characteristics and effects of the present invention, the conception, specific steps and technical effects of the present invention will be further illustrated in combination with the attached drawings below.

BRIEF DESCRIPTION OF THE DRAWINGS

FIG. 2A shows detection results of amplification of 100 copies (1%) of the mutant templates in the presence of 10,000 wild-type templates; FIG. 2B shows detection results of amplification of 10 copies (0.1%) of the mutant templates in the presence of 10,000 wild-type templates;

FIG. 3A shows detection results of amplifications of different templates without the presence of blocker; FIG. 3B shows detection results of amplifications of different templates using the blocker shown in SEQ ID NO: 1; FIG. 3C shows detection results of amplifications of different templates using the blocker shown in SEQ ID NO: 2; FIG. 3D shows detection results of amplifications of different templates using the blocker shown in SEQ ID NO: 3; FIG. 3E shows detection results of amplifications of different templates using the blocker shown in SEQ ID NO: 4;

FIG. 4A-FIG. 4D show the effect of different numbers of LNA modifications on amplification efficiency of mutant templates in an embodiment of the present invention; FIG. 4A shows amplification curves without using nucleic acid amplification blocker; FIG. 4B shows amplification curves using the nucleic acid amplification blocker shown in SEQ ID NO: 5; FIG. 4C shows amplification curves using the nucleic acid amplification blocker shown in SEQ ID NO: 6; and FIG. 4D shows amplification curves using the nucleic acid amplification blocker shown in SEQ ID NO: 7;

FIG. 5 shows the effect of the Tm value of the blocker on wild-type genome amplification in an embodiment of the present invention, in which LNA off represents a control test without the use of blocker;

FIG. 6A-FIG. 6F show amplification curves and melting curves using blockers with different lengths and different numbers of LNA modifications in an embodiment of the present invention; FIG. 6A shows amplification curves of a sample containing 100 copies (1%) of mutant templates; FIG. 6B shows amplification curves of a sample containing 10 copies (0.1%) of the mutant templates; FIG. 6C shows amplification curves of a sample containing pure wild-type templates; FIG. 6D shows the variation trend of cycle threshold (Ct) values of amplification; FIG. 6E shows melting curves of duplexes formed by the blocker binding to the mutant templates; FIG. 6F shows melting curves of duplexes formed by the blocker binding to the wild-type templates;

FIG. 7A shows the amplification curves of different samples including a sample containing pure wild-type templates, a sample containing 100 copies (1%) of mutant templates, and a sample containing 10 copies (0.1%) of mutant templates; FIG. 7B shows the melting curves of duplexes formed by two blockers respectively binding to the wild-type templates and the mutant templates, in which W represents the wild-type templates and M represents the mutant templates;

FIG. 8A shows amplification curves of a sample containing 100 copies (1%) of mutant templates; FIG. 8B shows amplification curves of a sample containing 10 copies (0.1%) of the mutant templates; FIG. 8C shows amplification curves of a sample containing pure wild-type templates; FIG. 8D shows the variation trend of cycle threshold (Ct) values of amplification; FIG. 8E shows melting curves of duplexes formed by the blocker binding to the mutant templates; FIG. 8F shows melting curves of duplexes formed by the blocker binding to the wild-type templates;

FIG. 10A shows the amplification curves of samples using the first primer 2 (SEQ ID NO: 28); FIG. 10B shows the amplification curves of samples using the first primer 3 (SEQ ID NO: 29); FIG. 10C shows the amplification curves of samples using the first primer 4 (SEQ ID NO: 30); where, LNA off represents no blocker is used; and the samples include a sample containing 10,000 copies of wild-type genomes (10,000 wt), a sample containing 100 copies (1%) of mutant templates, a sample containing 10 copies (0.1%) of mutant templates, and a blank control;

FIG. 11A shows the amplification curves of a sample containing 10,000 copies of wild-type templates, a sample containing 100 copies of mutant templates, a sample containing 10 copies of mutant templates and a negative control, with the blocker binding to S768I mutation site of each sample or without the use of the blocker; FIG. 11B shows the amplification curves of a sample containing 10,000 copies of wild-type templates, a sample containing 100 copies of mutant templates, a sample containing 10 copies of mutant templates and a negative control, with the blocker binding to T790M mutation site of each sample or without the use of the blocker; FIG. 11C shows the amplification curves of a sample containing 10,000 copies of wild-type templates, a sample containing 100 copies (1%) of mutant templates, a sample containing 10 copies (0.1%) of mutant templates and a positive control (a sample containing 50 copies of pure mutant templates), targeted for G719S/G719C mutation site of the EGFR.

DETAILED DESCRIPTION OF THE EMBODIMENTS

Figure 1:
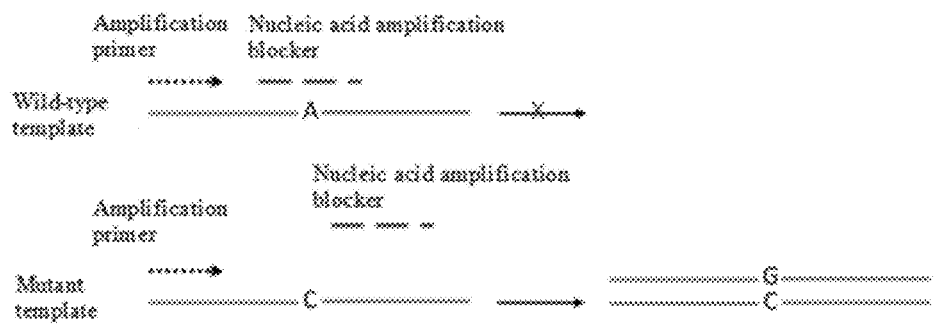
FIG. 1 is a schematic diagram showing the working process of the nucleic acid amplification blocker of the present invention.

The technical content of the present invention is further explained in combination with the following embodiments. The following embodiments are illustrative, not restrictive, and the scope of protection of the present invention cannot be limited by the following embodiments. The test methods used in the following embodiments are conventional unless otherwise specified. The materials, reagents, etc. used in the following embodiments are commercially available unless otherwise specified.

Experimental methods described in the following embodiments are generally performed under conventional conditions unless otherwise specified. For example, Sambrook et al, molecular cloning: performed under the conditions described in the laboratory manual 1989 by New York: Cold Spring Harbor Laboratory Press, or under the conditions as recommended by the manufacturer.

Definition

In this context, "allele" generally refers to a pair of genes that control relative traits at the same physical gene locus on homologous chromosomes. In some cases, alleles can correspond to single nucleotide differences (SNPs) at specific physical sites, or to the insertion or deletion of nucleotides (single or multiple nucleotides), etc.

In this context, the term "first allele variant" may represent an allele to be tested whose abundance is lower or much lower than that of the background allele. The first allele variant may be a low-abundance allele or a mutant allele in the sample. For example, for a given SNP or gene, the first allele variant may be less than $1/10$, $1/100$, or $1/1000$ in frequency relative to another allele variant.

In this context, the "second allele variant" may refer to the background allele whose abundance is higher than that of the variant to be detected, and the second allele variant may be either a high-abundance allele or a wild-type allele in the sample. For example, for a given SNP or gene, the second allele variant may be 10 times, 100 times, or 1000 times in frequency larger than another allele variant.

In this context, a "blocker" (also described as a "nucleic acid amplification blocker") is an oligonucleotide that can inhibit wild-type allele amplification by preferentially or tightly binding to the wild-type allele (or binding to the relatively high-abundance allele variant in the sample). This enables the mutant allele (or a relatively low-abundance or extremely low-abundance allele variant in the sample) to generate the target nucleic acid sequence amplicon of the mutant allele by amplification reaction.

In this context, "low abundance" means 10 to 100 copies of the first allele variant molecule in the background of 10,000 copies of the second allele variant.

In this context, the "Tm value of the blocker" refers to the Tm value of the blocker acquired by calculation. In some embodiments, a primer design software, i.e., IDTs Oligo Analyzer Tools, is used for the calculation. The "Tm value of the first primer" refers to the Tm value of the first primer obtained by calculation. In some embodiments, a primer design software, i.e., IDTs Oligo Analyzer Tools, is used for the calculation. In the following, "ΔTm" refers to the difference obtained from the Tm value of the blocker minus the Tm value of the first primer.

In this context, the "Tm value of the blocker binding to the second allele variant" and the "Tm value of the blocker binding to the first allele variant" are measured by the melting curve after synthetic single chain simulation. In the specific embodiment, for the single-base mutation site L861Q of EGFR, complementary chains 861W: TGGC-CAAACTGCTGGGTGCGGG (SEQ ID NO: 21, wild-type sequence) and 861M: TGGCCAAACAGCTGGGTGCGG (SEQ ID NO: 22, mutant sequence) are used to figure out the melting curve, wherein underlines represent SNP locations.

The Tm value of the blocker binding to the second allele variant (or wild type) is also referred to as "Tm1" below, and the Tm value of the blocker binding to the first allele variant (or mutant type) is also referred to as "Tm2" below. In the following, "ΔTm'" is the difference obtained from the Tm value (Tm1) of the blocker binding to the second allele variant (or wild type) minus the Tm value (Tm2) of the blocker binding to the first allele variant (or mutant type).

In this context, the "melting curve" refers to the curve of the degree to which the DNA double helix structure degrades with the increase of temperature.

An embodiment of the present invention provides a blocker, and the matching region of the blocker is located in the corresponding region of the second allele variant corresponding to the regions of the first allele variant amplified by the first primer and the second primer. The blocker is completely complementary to the second allele variant and contains at least one base mismatch with the first allele variant. The 3' end of the blocker is modified so that it can inhibit the primer extension reaction, enabling the blocker to inhibit the amplification of the second allele variant after the blocker binds to the second allele variant.

The difference (ΔTm) between the Tm value of the blocker and the Tm value of the first primer is adjusted by changing the number of LNA modifications, the LNA modification site and the length of the blocker. Moreover, the difference ΔTm' (ΔTm'=Tm1−Tm2) obtained from the Tm value (Tm1) of the blocker binding to the second allele variant minus the Tm value (Tm2) of the blocker binding to the first allele variant can also be adjusted by changing the number of LNA modifications, the LNA modification site and the length of the blocker. The Tm of the blocker is the key to inhibit the second allele variant, and the ΔTm decides whether the second allele variant can be inhibited. The second allele variant can be effectively inhibited when ΔTm is greater than or equal to 7.5° C. ΔTm' decides whether the blocker can inhibit the amplification of the first allele variant. The larger ΔTm' results in the less inhibited amplification of the first allele variant and the higher amplification efficiency.

In some embodiments, ΔTm is controlled between 7.5° C. and 12° C. in order to better inhibit the second allele variant and concurrently reduce the preparation cost of the blocker. In other embodiments, ΔTm is controlled between 8° C. and 10° C.

From the cost perspective, the ΔTm range mentioned above and maximum ΔTm' are achieved by controlling the number of LNA modifications, the LNA modification site and the length of the blocker in some embodiments. The base of the blocker where a mismatch is formed with the first allele variant is located in the central region of the blocker (in some embodiments, the central region is a segment having a length approximately one third of the length of the blocker and located in the middle of the blocker). The principles of performing LNA modification are as follows:

1) LNA modification is conducted on the base of the blocker where a mismatch is formed with the first allele variant; 2) LNA modification is not performed on the 3'-terminal base and the 5'-terminal base of the blocker.

In some embodiments, the number of LNA modifications of the blocker is greater than or equal to 4 and less than or equal to 6; the length of the blocker is greater than or equal to 14 bases and less than or equal to 16 bases. The blocker meeting the requirements of the ΔTm, the number of LNA modifications and the length of the blocker and having the maximum ΔTm' can inhibit the amplification of the second allele variant effectively but does not inhibit the amplification of the first allele variant, at the same time, the cost of design and manufacture can be effectively controlled.

Another specific embodiment of the present invention provides a method for designing a blocker. The core idea of the design is: for the detection of mutant genomes, especially for single-base mutation detection, it is vital to inhibit the amplification of high-abundance wild-type genomes, which requires blocking primer extension. In this way, the blocker has to possess absolute superiority in binding to wild-type genome templates in the annealing stage. Therefore, the blocker should have larger Tm and concentration than primers to prevent the primers from binding to wild-type templates and triggering amplification in the annealing stage. While continuing to increase Tm can inhibit the amplification of wild-type templates, it may also inhibit the amplification of ultra-low-abundance mutant templates. Unlike the binding of the blocker to the wild-type templates, the binding of the blocker to the mutant templates may produce a base mismatch, which reduces the binding affinity of the blocker to the templates. But if the Tm of the blocker is too high and the reduction in the binding affinity caused by the base mismatch is limited, the blocker will compete with the primers to bind to the mutant templates in the annealing phase, resulting in a decrease in the efficiency of primer to amplify the mutated templates, and even a completely inhibition of the amplification. Therefore, to ensure the amplification efficiency, it is necessary to make the binding affinity between the blocker and the mutant templates as low as possible on the premise of maintaining a certain Tm (as long as ensuring that the wild-type genomes are inhibited), so as to reduce the competitive effect between the blocker and the primers, and ensure the amplification efficiency. Therefore, the Tm value of the blocker should be controlled within a suitable range. The design method of this implementation mode is to use the most economical and simplest means to make the affinity between the blocker and the mutant templates lower than that between the primer and the mutant templates, thereby ensuring that the primers are completely unaffected, and maintaining the highest amplification efficiency, so as to achieve the efficient detection of the mutation genes.

This method uses the least LNA and the shortest chain segment to construct the blocker that meets the requirement of Tm. In this method, the blocker is completely complementary to the second allele variant, and contains a mismatch with the first allele at the mutation site. In the selection of the binding site of the blocker, the base that has a mismatch with the first allele at the mutation site is located in the central region of the blocker (in some embodiments, the central region is a segment having a length approximately one third of the length of the blocker and located in the middle of the blocker). In this regard, when designing the blocker, the initial length of the blocker was set to be 14 bases, and an initial sequence of the blocker was determined. Then LNA modifications were performed on the initial sequence of the blocker, and the initial number of LNA modifications was 4. After a combination of the LNA modifications was identified, the blocker was examined whether there is a hairpin structure and a self-folding structure (in particular, a hairpin structure with an LNA-LNA-matching). If there was no hairpin structure and self-folding structure, the melting temperature was calculated. If ΔTm was less than 7.5° C., the length of the blocker was increased by 1 base length, and/or the number of LNA modifications was increased by one, to make ΔTm≥7.5° C. If the blocker had a hairpin structure and a self-folding structure in the process, or the length of the blocker reached to 16 base length and the number of LNA modifications reached to 6, the blocker with ΔTm greater than or equal to 7.5° C. still cannot be obtained, then the setting position of the blocker should be changed to start the design again.

The principles of performing the LNA modification are as follows: 1) LNA modification is performed on the base where a mismatch is formed with the first allele variant; 2) The remaining LNA modifications cannot be conducted on the 3'-terminal base and the 5'-terminal base of the blocker.

In some specific embodiments, the concentrations of primers, magnesium ions, sodium ions and dNTP in the reaction system of the amplification reaction may not be considered in the calculation of the melting temperature. However, it is preferable to consider the concentrations of primers, magnesium ions, sodium ions and dNTP in the reaction system of the amplification reaction, so that the obtained melting temperature is more consistent with the actual situation, thus a better blocker can be adjusted and designed.

In some specific embodiments, the first primer needs to be identified first or the first primer, the second primer and the detection probe need to be determined first, then the design for the blocker is performed. Tm of the first primer is larger than or equal to 60° C.

The advantages of the above design method are as follows. Whether a blocker can achieve the effect of inhibiting the amplification of the second allele variant, but not inhibiting the amplification of the first allele variant is investigated by calculating the Tm value instead of performing complicated experiments, thus saving time cost. In addition, the above method controls the number of LNA modifications (as little as possible), the LNA modification site and the length of the blocker (as short as possible), thus reducing the preparation cost of the blocker.

In the embodiments, the single-base mutation site L861Q of the EGFR was used as a study model to verify the design principles of the blocker. The primers, blockers and detection probes were synthesized using a solid phase method by Sangon Biotech (Shanghai) Co., Ltd.

In the embodiments, the Tm value of the blocker and the Tm value of the first primer were calculated by a primer design software, i.e., Oligo Analyzer Tools of IDT. In Embodiments 1-2, the effects of concentrations of blockers, magnesium ions, sodium ions, and dNTP were not taken into consideration during the calculation. In Embodiments 3-9, the following concentrations were set during the calculation: 1.5 μM of blockers, 1.5 mM of magnesium ions, 0 mM of sodium ions, and 0.3 mM of dNTP, which was closer to the actual amplification reaction. When calculating the Tm of the first primer as shown in SEQ ID NO: 9 by the primer design software, i.e., Oligo Analyzer Tools of IDT, the following concentrations were set during the calculation: 1.5 μM of blockers, 1.5 mM of magnesium ions, 0 mM of sodium ions, and 0.3 mM of DNTP. The Tm value of the first primer as shown in SEQ ID NO: 9 was calculated to be 66° C.

In Embodiments 3-7, the first primer as shown in SEQ ID NO: 9, the second primer as shown in SEQ ID NO: 8, and the TaqMan probe as shown in SEQ ID NO: 10 were used for the amplification reaction and detection. In Embodiments 3-9, the templates for amplification include: the wild-type genome derived from A549 cell genome (derived from ATCC, No: ATCCCCL-185); the mutant genome that is a mutant plasmid, specifically EGFR L861Q as shown in SEQ ID NO: 23, EGFR T790M as shown in SEQ ID NO: 24, EGFR S768I as shown in SEQ ID NO: 25, EGFR G719S as shown in SEQ ID NO: 26 and EGFR G719C as shown in SEQ ID NO: 27 (purchased from Sangon Biotech (Shanghai) Co., Ltd.); the sample containing 0.1% mutant genome (10 copies of mutant genomes) that is prepared by adding 10 copies of mutant plasmid to 10,000 copies of wild-type genome; the sample containing 1% mutant genome (100 copies of mutant genome) that is prepared by adding 100 copies of mutant plasmid into 10,000 copies of wild-type genome; the sample containing 10 copies of pure mutant genome without wild-type genome; and the sample containing 100 copies of mutant genome without wild-type genome.

PCR amplification system is specifically shown as follows:

| | |
|---|---|
| PCR mix (2×) | 10 μL |
| First primer (5 μM) | 0.6 μL |
| Second primer (10 μM) | 0.3 μL |
| Blocker (50 μM) | 0.6 μL |
| TaqMan probe (5 μM) | 0.4 μL |
| ddH$_2$O | 3.4 μL |
| DNA template | 5 μL |
| Total | 20.3 μL |

Note:
* In the experiment without blocker, only probe was added, and DDH$_2$O was used as supplement. When preparing the PCR reaction solution, each tube is configured or filled with 15 μL of the PCR reaction solution.

The qPCR amplification conditions were as follows: pre-denaturation at 95° C. for 2 minutes; pre-amplification: 15 cycles of denaturation at 95° C. for 1 second, denaturation at 70° C. for 20 seconds, and denaturation at 60° C. for 20 seconds; signal acquisition: 30 cycles of denaturation at 95° C. for 1 second, denaturation at 70° C. for 20 seconds, and denaturation at 60° C. for 20 seconds.

Detection method: the qPCR was performed using LightCycler® 96 system (Roche), and an absolute quantitative analysis was performed using system default baseline.

In the embodiments, when determining the melting curve, the following reaction system was prepared:

| | |
|---|---|
| PCR mix (2×) | 10 μL |
| Blocker (10 μM) | 3 μL |
| Template (50 μM) | 0.6 μL |
| EvaGreen(20×) | 1 μL |
| ddH$_2$O | 5.4 μL |
| Total | 20 μL |

The amplification process for the melting curve was as follows: 1 cycle of pre-incubation at 55° C. for 10 minutes; 1 cycle of denaturation at 95° C. for 10 seconds, 55° C. for 50 seconds, and 97° C. for 1 second (10 readings/° C.).

Embodiment 1 (Effect of Different Numbers of LNA Modifications on Mutation Amplification Efficiency)

1. Preparation of LNA-Modified Nucleic Acid Amplification Blocker

Keeping the constant annealing temperature of the nucleic acid amplification blocker, the effect of different numbers of LNA modifications on the amplification efficiency of mutant template was verified by changing the number and the length of LNA modifications. Taking EGFR L861Q mutation as an example, different nucleic acid amplification blockers were designed and their sequences are shown in Table 1 (SEQ ID NO: 1 through SEQ ID NO: 4).

2. PCR Amplification

Targeted for the EGFR L861Q mutation to be detected, a pair of primers was designed for amplification, and their sequences are shown in Table 2 (SEQ ID NO: 8 to SEQ ID NO: 9). The detection was conducted by using TaqMan probe, and its sequence is shown in Table 2 (SEQ ID NO: 10).

2.1. Template DNA extraction: template DNA was extracted from a patient's tissue sample using other commercial kit.

2.2. Synthesis of PCR primers: the synthesis method is a conventional DNA synthesis method.

2.3 Preparation of PCR reaction solution: 15 μL/person of PCR reaction solution was prepared, in which the concentrations of upstream and downstream primers were respectively 0.2 μmol/L, the concentrations of probe and nucleic acid amplification blocker were respectively 0.1 μmol/L, the concentration of Taq DNA polymerase was 1 U/μL, 1×PCR buffer, $MgCl_2$ was 1.5 mmol/L, the concentration of dNTP was 0.2 mmol/L, and the concentration of template DNA was 1-10 ng/μL.

2.4 PCR amplification: the reaction procedure of PCR amplification was: pre-denaturation at 95° C. for 5 minutes; 35 cycles of denaturation at 95° C. for 30 seconds, 70° C. for 20 seconds, renaturation at 60° C. for 30 seconds (fluorescence signal acquisition), and extension at 72° C. for 30 seconds. The product obtained after PCR amplification contains a patient's DNA fragments.

3. Result Analysis

Figure 2A:
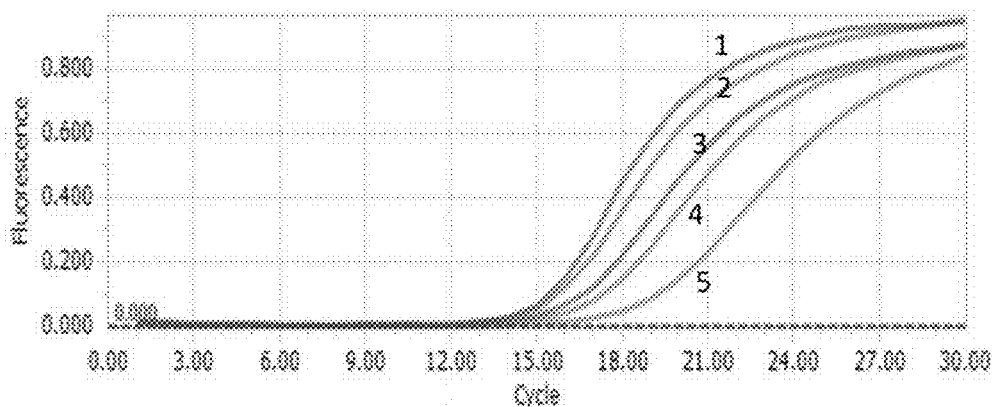
FIG. 2A-FIG. 2B show the effect of the number and the length of LNA modifications on amplification efficiency of mutant templates under constant annealing temperature in an embodiment of the present invention.
Figure 2B:
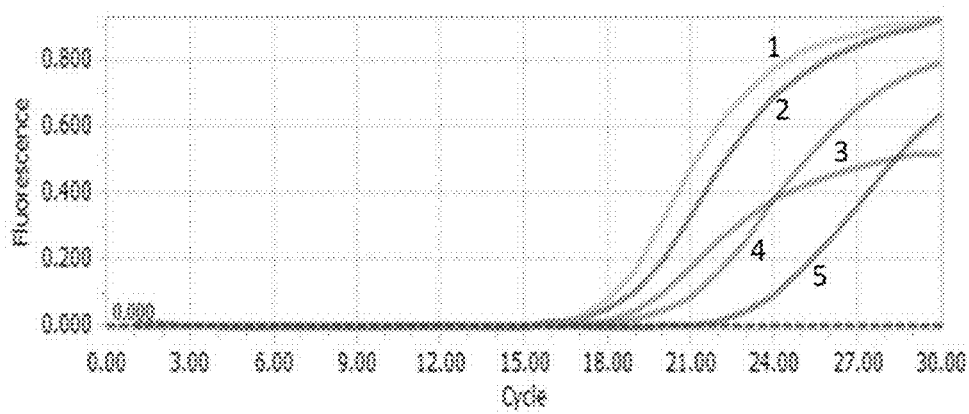

Fluorescent quantitative PCR results were analyzed using the corresponding software, and baseline and threshold were set in the FAM channel. The threshold was set in the low-fluorescence signal exponential amplification region to determine the corresponding Ct value. The detection results were shown in FIG. 2A-FIG. 2B, where, 1 represents the amplification curves without nucleic acid amplification blocker; 2 represents the amplification curves using the nucleic acid amplification blocker as shown in SEQ ID NO: 4; 3 represents the amplification curves using the nucleic acid amplification blocker as shown in SEQ ID NO: 3; 4 represents the amplification curves using the nucleic acid amplification blocker as shown in SEQ ID NO: 2; and 5 represents the amplification curves using the nucleic acid amplification blocker as shown in SEQ ID NO: 1. FIG. 2A shows the detection results of amplifying 100 copies (1%) of mutant template amplified in the background of 10,000 wild-type template; FIG. 2B shows the detection results of amplifying 10 copies (0.1%) of mutant template in the background of 10,000 wild-type template. The results show that when the Tm value reaches 65° C., the inhibition effect of LNA on the mutant template decreases gradually with the increase of the number of LNA modifications from 0 to 3 and the decrease of the length from 21 bp to 18 bp.

Figure 3A:
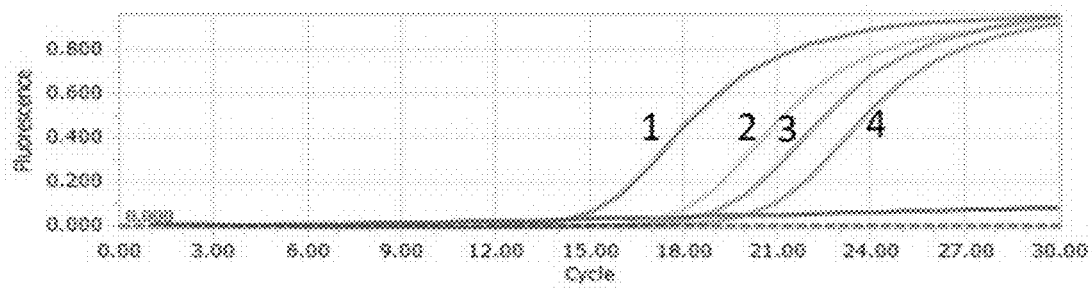
FIG. 3A-FIG. 3E show the effect of the number and the length of LNA modifications on inhibition of amplification of wild-type templates under constant annealing temperature in an embodiment of the present invention.
Figure 3B:
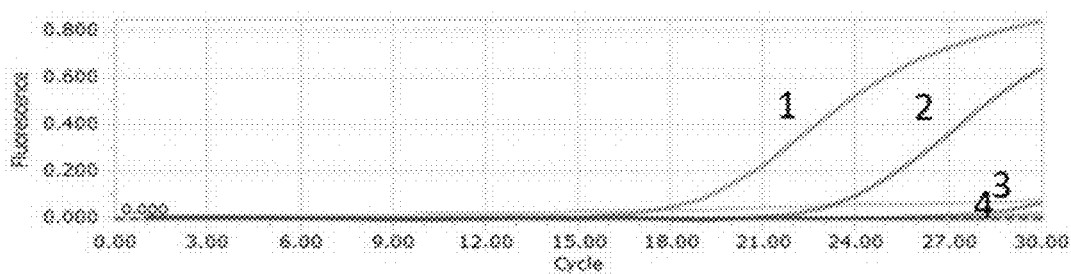
Figure 3C:
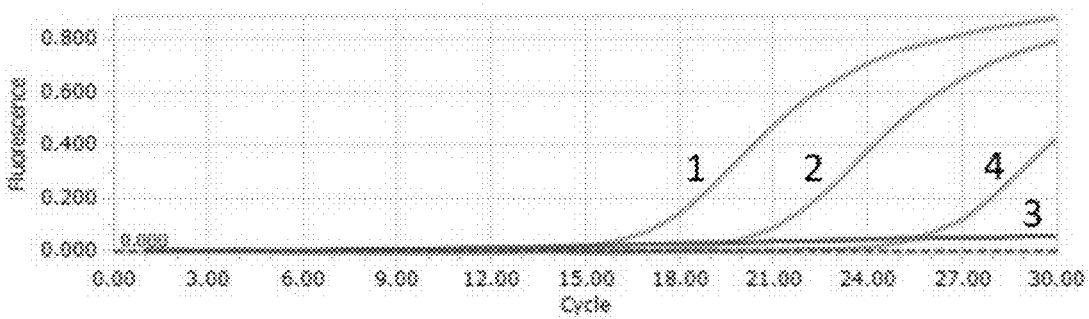
Figure 3D:
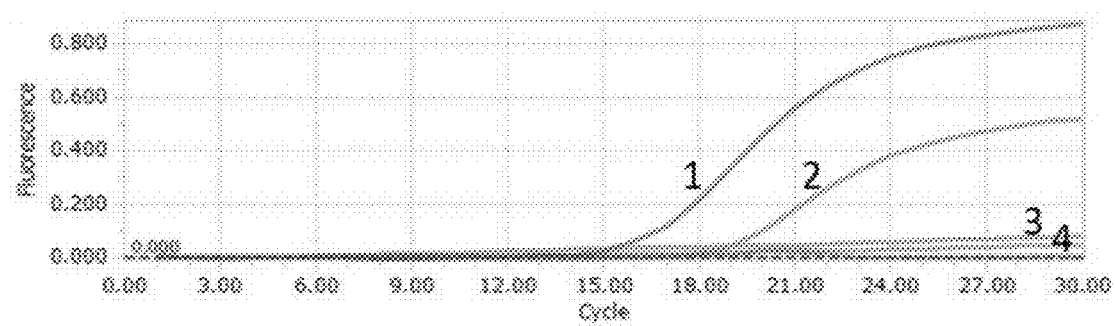
Figure 3E:
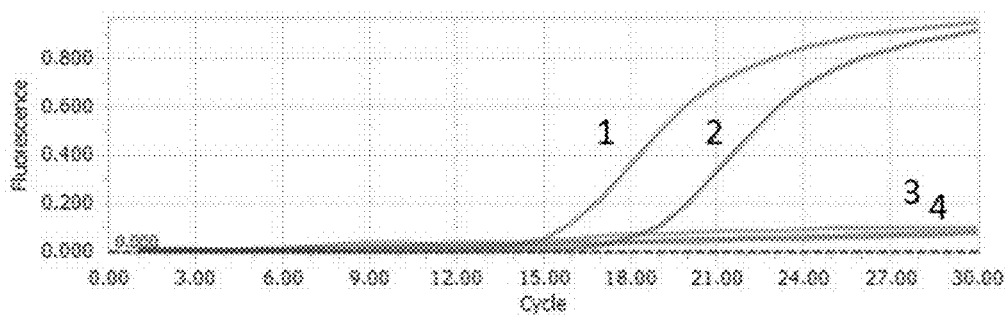

The inhibitory effect of different lengths and numbers of LNA modifications on wild-type genomes is shown in FIG. 3A-FIG. 3E. FIG. 3A shows the detection results when amplifying different templates in the absence of blocker; FIG. 3B shows the detection results when amplifying different templates using the nucleic acid amplification blocker as shown in SEQ ID NO: 1; FIG. 3C shows the detection results when amplifying different templates using the nucleic acid amplification blocker as shown in SEQ ID NO: 2; FIG. 3D shows the detection results when amplifying different templates using the nucleic acid amplification blocker as shown in SEQ ID NO: 3; FIG. 3E shows the detection results when amplifying different templates using the nucleic acid amplification blocker as shown in SEQ ID NO: 4. In the figures, the templates used are as follows: 1 represents 100 copies (1%) of mutant template amplified in the background of 10,000 wild-type template; 2 represents 10 copies (0.1%) of mutant template amplified in the background of 10,000 wild-type template; 3 represents 5,000 wild-type template; and 4 represents 10,000 wild-type template.

Embodiment 2 (Effect of LNA with Same Length but Different LNA Modification Sites)

1. Preparation of LNA-Modified Nucleic Acid Amplification Blocker

Keeping the constant length of the nucleic acid amplification blocker and the unchanged number of LNA modifications, the effect of LNA modification sites on the amplification efficiency of mutant template was verified by changing the LNA modification sites. Targeted for EGFR L861Q mutation, different nucleic acid amplification blockers were designed and their sequences are shown in Table 1 (SEQ ID NO: 5 through SEQ ID NO: 7).

2. PCR Amplification

Targeted for the EGFR L861Q mutation to be detected, a pair of primers was designed for amplification, and their sequences are shown in Table 2 (SEQ ID NO: 8 to SEQ ID NO: 9). The detection was conducted by using TaqMan probe, and its sequence is shown in Table 2 (SEQ ID NO: 10).

2.1. Template DNA extraction: template DNA was extracted from a patient's tissue sample using other commercial kit.

2.2. Synthesis of PCR primers: the synthesis method is a conventional DNA synthesis method.

2.3 Preparation of PCR reaction solution: 15 μL/person of PCR reaction solution was prepared, in which the concentrations of upstream and downstream primers were respectively 0.2 μmol/L, the concentrations of probe and nucleic acid amplification blocker were respectively 0.1 μmol/L, the concentration of Taq DNA polymerase was 1 U/μL, the concentrations of 1×PCR buffer and $MgCl_2$ were respectively 1.5 mmol/L, the concentration of dNTP was 0.2 mmol/L, and the concentration of template DNA was 1-10 ng/μL.

2.4 PCR amplification: the reaction procedure of PCR amplification was: pre-denaturation at 95° C. for 5 minutes; 35 cycles of denaturation at 95° C. for 30 seconds, denaturation at 70° C. for 20 seconds, renaturation at 60° C. for 30 seconds (fluorescence signal acquisition), and extension at 72° C. for 30 seconds. The product obtained after PCR amplification contains a patient's DNA fragments to be detected.

3. Result Analysis

Figure 4A:
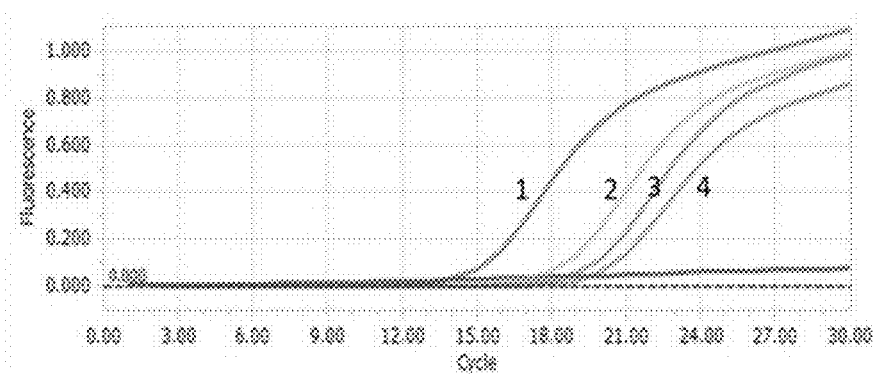
Figure 4B:
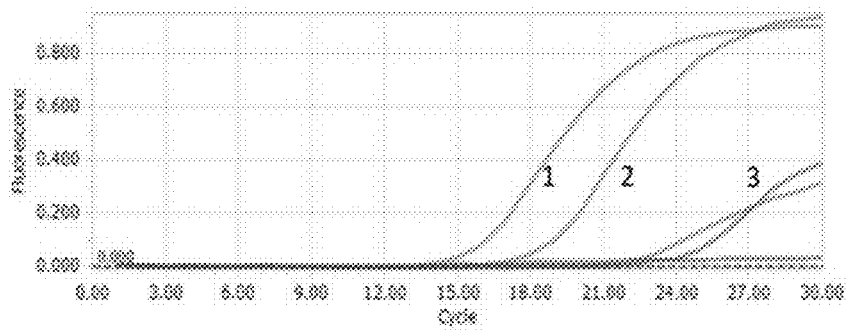
Figure 4C:
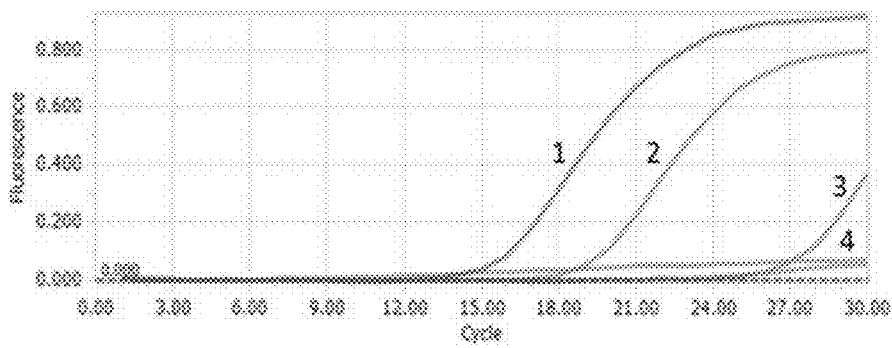

Fluorescent quantitative PCR results were analyzed using the corresponding software, and baseline and threshold were set in the FAM channel. The threshold was set in the low-fluorescence signal exponential amplification region to determine the corresponding Ct value. The detection results were shown in FIG. 4A-FIG. 4D, where, 1 represents the detection results when amplifying 100 copies (1%) of mutant template in the background of 10,000 wild-type template; 2 represents the detection results when amplifying 10 copies (0.1%) of mutant template in the background of 10,000 wild-type template; 3 represents 10,000 wild-type template; and 4 represents 5,000 wild-type template. FIG. 4A shows the amplification curves without nucleic acid amplification blocker; FIG. 4B shows the amplification curves using the nucleic acid amplification blocker as shown in SEQ ID NO: 5; FIG. 4C shows the amplification curves using the nucleic acid amplification blocker as shown in SEQ ID NO: 6; FIG. 4D shows the amplification curves using the nucleic acid amplification blocker as shown in SEQ ID NO: 7. The results show that different LNA modification sites can effectively change the annealing temperature of nucleic acid amplification blocker. Moreover, as the annealing temperature increases, the nucleic acid amplification blocker shows stronger and stronger inhibitory effect on wild-type template while has no obvious change in inhibitory effect on the amplification of mutant template.

TABLE 1

Sequences of nucleic acid amplification blockers with different lengths but relatively close annealing temperatures

| SEQ ID NO. | Tm (° C.) | Length | Sequence (5'-3') | Number of LNA modifications |
|---|---|---|---|---|
| 1 | 65.7 | 21 | CCGCACCCAGCAGTTTGGCCA | 0 |
| 2 | 65.5 | 20 | CGCACCCAGCAGTTTGGCCA | 1 |
| 3 | 65.2 | 19 | GCACCCAGCAGTTTGGCCA | 2 |
| 4 | 65.9 | 18 | CACCCAG*C*A*G*TTTGGCCA | 3 |
| 5 | 63 | 15 | ACCCA*GCA*GTTTGGC | 4 |
| 6 | 65.1 | 15 | ACCCAG*C*AGTTT*GG*C | 4 |
| 7 | 66.6 | 15 | A*C*CCAGCAGTT*T*GGC | 4 |

Note:
Underlines represent mutation sites, and letters in bold italics represent LNA modification sites.

TABLE 2

Sequences of primers required for PCR amplification

| SEQ ID NO: | Sequence (5'-3') |
|---|---|
| 8 | CTTGGTGCACCGCGACCTG |
| 9 | TCTTTCTCTTCCGCACCCAGCT |
| 10 | FAM-CACGTGTGCCGCCTGC-MGB |

Embodiment 1 and Embodiment 2 show that the inhibitory effect of blocker on the amplifications of wild-type template and mutant template may follow a specific rule based on the change in the Tm value of the blocker, the number of LNA modifications, the LNA modification site and the length of the blocker. Therefore, the following embodiments propose a general design principle with low cost for rapidly designing a blocker with minimum length and minimum number of LNA modifications by comprehensively considering the effects of the Tm value, the number of LNA modifications, the LNA modification site and the length of the blocker.

Embodiments 3 (Effect of Tm Value of Blocker on Wild-Type Genome Amplification)

In this embodiment, the effect of ΔTm on the amplification of wild-type genomes in samples was studied by setting blockers with different Tm values (calculated Tm values).

1. Blockers: the blockers designed with different Tm values were as shown in Table 3.

TABLE 3

Blockers with different Tm values and their effects on wild-type genome amplification

| Blocker name | SEQ ID NO: | Sequence (5'-3') | Length | Number of LNA modifications | Tm value (° C.) of blocker | ΔTm (° C.) | Whether is wild-type genome amplification fully inhibited |
|---|---|---|---|---|---|---|---|
| 861 LNA1 | 11 | *CAGCAGTTTGG* | 11 | 6 | 58.1 | −7.9 | No |
| 861 LNA2 | 12 | *CCAGCAGTTTGG* | 12 | 6 | 66.7 | 0.7 | No |
| 861 LNA3 | 13 | *CCCAGCAGTTTGG* | 13 | 7 | 70.9 | 4.9 | No |
| 861 LNA4 | 14 | *ACCCAGCAGTTTGG* | 14 | 7 | 78.4 | 12.4 | Yes |
| 861 LNA5 | 15 | *CACCCAGCAGTTTGG* | 15 | 8 | 78.1 | 12.1 | Yes |
| 861 LNA7 | 16 | CCGCACCCAGCAGTTTGGCCA | 21 | 0 | 73.5 | 7.5 | Yes |
| 861 LNA10 | 4 | CACCCAG*CA*GTTTGGCCA | 18 | 3 | 74.7 | 8.7 | Yes |
| 861 LNA11 | 5 | ACCCA*GCA*GTTTGGC | 15 | 4 | 72.4 | 6.4 | No |
| 861 LNA12 | 6 | ACCCAG*CA*GTTT*GG*C | 15 | 4 | 74.9 | 8.9 | Yes |

Note:
1) Underlines represent the bases corresponding to the mutation sites, and letters in bold italics represent the LNA modification sites.
2) The Tm value of the blocker is obtained by calculation.

2. Result analysis: Fluorescent quantitative PCR results were analyzed using the corresponding software, and baseline and threshold were set in the FAM channel. The threshold was set in the low-fluorescence signal exponential amplification region to determine the corresponding Ct value. The detection results were shown in Table 3 and FIG. 5. The templates used contained 10,000 copies of wild-type genomes. As can be seen from FIG. 5, the amplification of wild-type genome was normally conducted in the absence of blocker (LNA off). However, as the Tm value of the blocker continuously increased, the blocker showed increasingly strong inhibition on wild-type genome amplification until reaching complete inhibition. Moreover, 10,000 copies of wild-type genome could be completely inhibited when ΔTm reached 7.5° C., otherwise, amplification may occur in the wild-type genome below this temperature.

Therefore, the Tm value of the blocker should be set as the key factor to inhibit wild-type genome amplification in the subsequent design of a low-cost blocker. ΔTm should be greater than or equal to 7.5° C.

Embodiments 4 (Effects of the Length of the Blocker and the Number of LNA Modifications on the Amplification of Mutant Genomes)

In this embodiment, the effect of ΔTm' on the amplification of mutant genomes in samples was studied by setting blockers with different lengths and different numbers of LNA modifications.

1. Blockers: the blockers designed with different lengths and different numbers of LNA modifications are shown in Table 4.

TABLE 4

Blockers with different lengths and numbers of LNA modifications

| Blocker name | SEQ ID NO: | Sequence (5'-3') | Length | Number of LNA modifications | Tm value (° C.) of blocker | ΔTm (° C.) | Tm1 (° C.) | Tm2 (° C.) | ΔTm' (° C.) |
|---|---|---|---|---|---|---|---|---|---|
| 861 LNA7 | 16 | CCGCACCCAGCAGTTTGGCCA | 21 | 0 | 73.5 | 7.5 | 77.35 | 72.89 | 4.46 |
| 861 LNA8 | 2 | CGCACCCAGC*A*GTTTGGCCA | 20 | 1 | 73.7 | 7.7 | 77.87 | 71.41 | 6.46 |
| 861 LNA9 | 3 | GCACCCAGC*A*TTTGGCCA | 19 | 2 | 73.7 | 7.7 | 76.54 | 69.08 | 7.46 |
| 861 LNA10 | 4 | CACCCAG*CA*GTTTGGCCA | 28 | 3 | 74.7 | 8.7 | 77.64 | 68.62 | 9.02 |

Note:
1) Underlines represent the bases corresponding to the mutation sites, and letters in bold italics represent the LNA modification sites.
2) The Tm value of the blocker is obtained by calculation, and the Tm1 and the Tm2 are determined by melting curves.

Figure 6C:
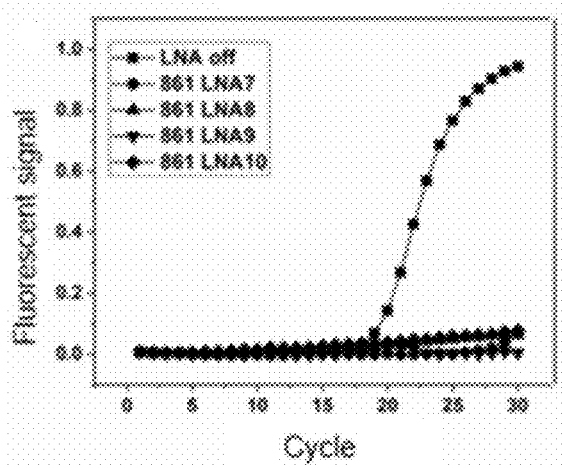
Figure 6D:
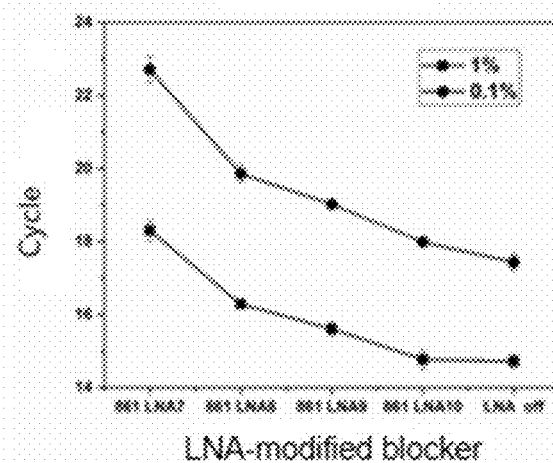
Figure 6E:
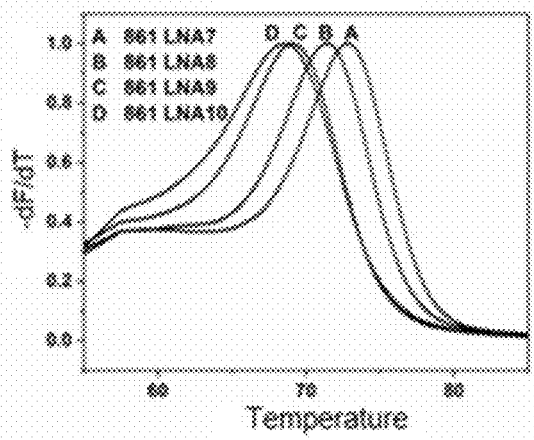
Figure 6F:
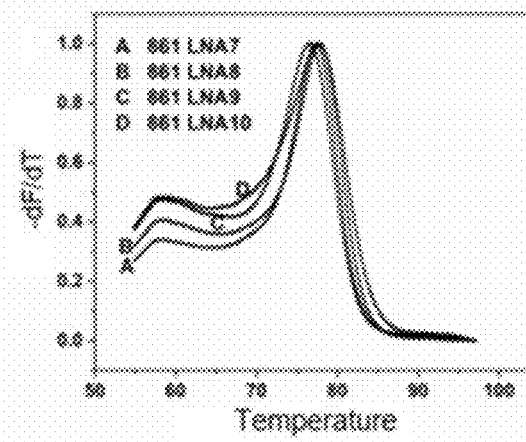

2. Result analysis: as shown in FIG. 6C, when ΔTm reached 7.5° C., the amplification of 10,000 copies of wild-type genome could be completely inhibited. As shown in FIGS. 6A and 6B, when the length of the blocker gradually decreased and the number of LNA modifications gradually increased, the amplification efficiency of the mutant genome increased accordingly. It was predictable that, to some extent, the amplification efficiency of the mutant genome was almost comparable to that without using the blocker. FIGS. 6E and 6F's melting curves showed that when the Tm of the blocker and the Tm of the blocker binding to the wild-type genome were almost the same (see the Tm and Tm1 columns in Table 4), as the number of LNA modifications increased, the Tm (i.e., Tm2) of the blocker binding to the mutant gene gradually decreased (namely, ΔTm' gradually increased). Combining the melting curve with the amplification curve, it is clear that the lower the Tm value (Tm2) of the blocker binding to the mutant gene (namely, the greater the ΔTm'), the smaller the interference on the amplification of the mutant genome and the higher the amplification efficiency.

Therefore, it is necessary to consider how to minimize the Tm value (Tm2) of the blocker binding to the mutant gene, i.e., maximizing the ΔTm', while controlling the cost when figuring out the method of rapid design of low-cost blockers.

Embodiments 5 (Effect of Mismatch Site of Blocker being Modified with or without LNA)

In this embodiment, the effect of the base of blocker where a mismatch was formed with the mutation site of mutant genome being modified with or without LNA on the amplification was studied.

1. Blockers: the designed blockers are shown in Table 5.

TABLE 5

Blockers with mismatch sites being modified with or without LNA.

| Blocker name | SEQ ID NO: | Sequence (5'-3') | Length | Number of LNA modifications | Tm value (° C.) of blocker | ΔTm (° C.) | Tm1 (° C.) | Tm2 (° C.) | ΔTm' (° C.) |
|---|---|---|---|---|---|---|---|---|---|
| 861 LNA4 | 14 | ACCCAG*C*A*G*TT*TG* | 14 | 7 | 78.4 | 12.4 | 78.51 | 68.31 | 10.2 |
| 861 LNA6 | 17 | *CA*CCCAGC*A*GTT*TG*G | 15 | 7 | 75.2 | 9.2 | 76.19 | 69.23 | 6.96 |

Note:
1) Underlines represent the bases corresponding to the mutation sites, and letters in bold italics represent the LNA modification sites.
2) The Tm value of the blocker is obtained by calculation, and the Tm1 and the Tm2 are determined by melting curves.

Figure 7A:
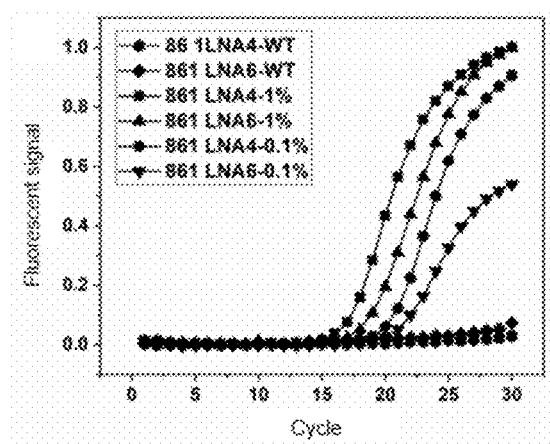
FIG. 7A-FIG. 7B show amplification curves and melting curves in the case of the mismatch base of the blocker being or being not modified with LNA in an embodiment of the present invention.
Figure 7B:
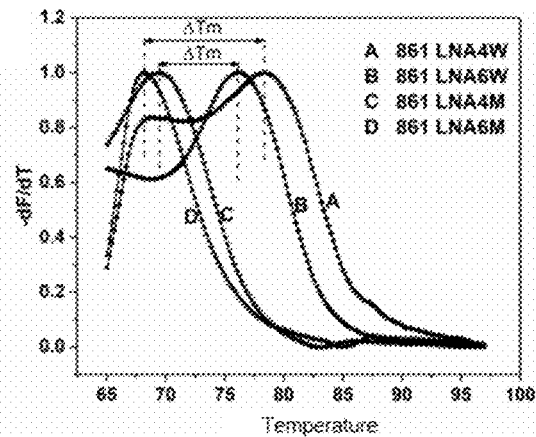

2. Result analysis: as shown in FIG. 7A, two blockers modified with LNA could inhibit the amplification of wild-type genes completely, but the blocker with mutation site being modified by LNA had a higher amplification efficiency, while the blocker with mutation site being not modified by LNA would inhibit the amplification of the mutant gene. The melting curves (FIG. 7B) showed that when the mutation site was modified by LNA, the Tm value (Tm2) of the blocker binding to the mutant genes would be more significantly reduced, ΔTm' was larger, and thus the mutant templates were less inhibited.

Therefore, it is necessary to modify the mismatch base with LNA in the blocker when developing a method of rapidly designing low-cost blockers.

Embodiments 6 (Research on the Blocker with Optimal Status of Minimum Length and Least LNA Modification)

In this embodiment, the effects of the length of the blocker and the number of LNA modifications on amplification were mainly studied.

1. Blockers: the designed blockers are shown in Table 6.

TABLE 6

Blockers with different lengths and different numbers of LNA modifications

| Blocker name | SEQ ID NO: | Sequence (5'-3') | Length | Number of LNA modifications | Tm value (° C.) of blocker | ΔTm (° C.) | Tm1 (° C.) | Tm2 (° C.) | ΔTm' (° C.) |
|---|---|---|---|---|---|---|---|---|---|
| 861 LNA10 | 4 | CACCCAG*CA*GTTTGGCCA | 18 | 3 | 74.7 | 8.7 | 77.64 | 68.62 | 9.02 |
| 861 LNA11 | 5 | ACCCAG*CA*GTTTGGC | 15 | 4 | 72.4 | 6.4 | 75.07 | 63.71 | 11.36 |
| 861 LNA12 | 6 | ACCCAG*CA*GTTT*GG*C | 15 | 4 | 74.9 | 8.9 | 75.47 | 64.17 | 11.3 |

Note:
1) Underlines represent the bases corresponding to the mutation sites, and letters in bold italics represent the LNA modification sites.
2) The Tm value of the blocker is obtained by calculation, and the Tm1 and the Tm2 are determined by melting curves.

Figures 8A, 8B, 8C:
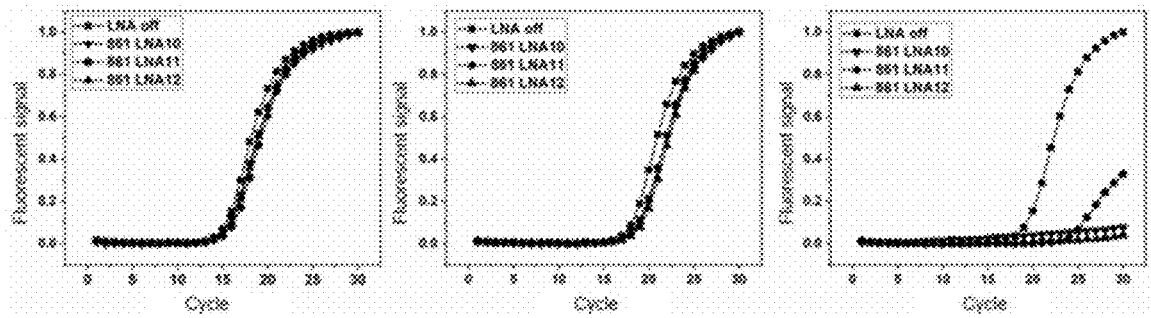
FIG. 8A-FIG. 8F show amplification curves and melting curves using blockers with different lengths and different numbers of LNA modifications in an embodiment of the present invention.
Figures 8D, 8E, 8F:
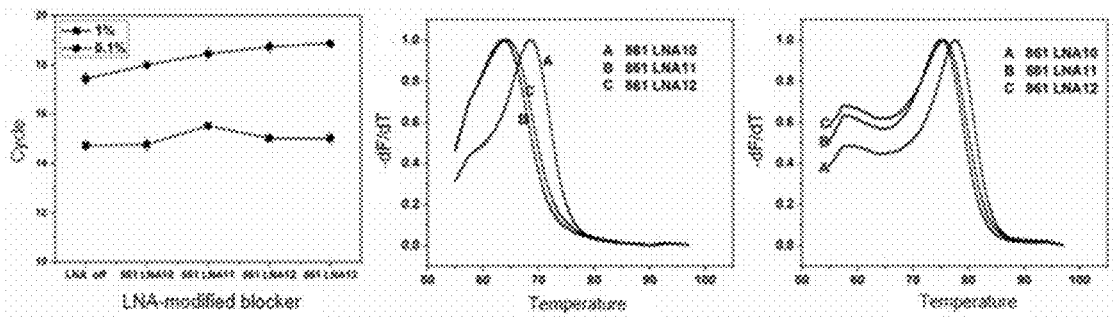

3. Result analysis: as shown in FIG. 8C, 861 LNA11 could not inhibit the amplification of wild-type genome completely because its ΔTm was less than 7.5° C., but the other two blockers could inhibit the amplification of wild-type genome completely because their ΔTm were greater than 7.5° C. Due to the values of ΔTm' were all relatively large, as shown in FIGS. 8A and 8B, the three blockers almost had no effect on the amplification of mutant genome. As shown in FIG. 8E and FIG. 8F, the melting temperatures of the three blockers binding to mutant genomes decreased significantly compared to that binding to wild-type genomes.

Embodiment 7 (Method for Rapid Design of Low-Cost Blockers)

Based on the principles outlined above, this embodiment provides a method for a rapid design of a low-cost blocker. Low cost includes: low experimental cost required to determine the blocker, and low cost for synthesizing the blocker.

The general rule of blocker design is: blocker and wild-type template are completely complementary, there is at least one base mismatch between blocker and mutant template, and the base where the mismatch is formed with mutant template is set in the central region of blocker.

Figure 9:
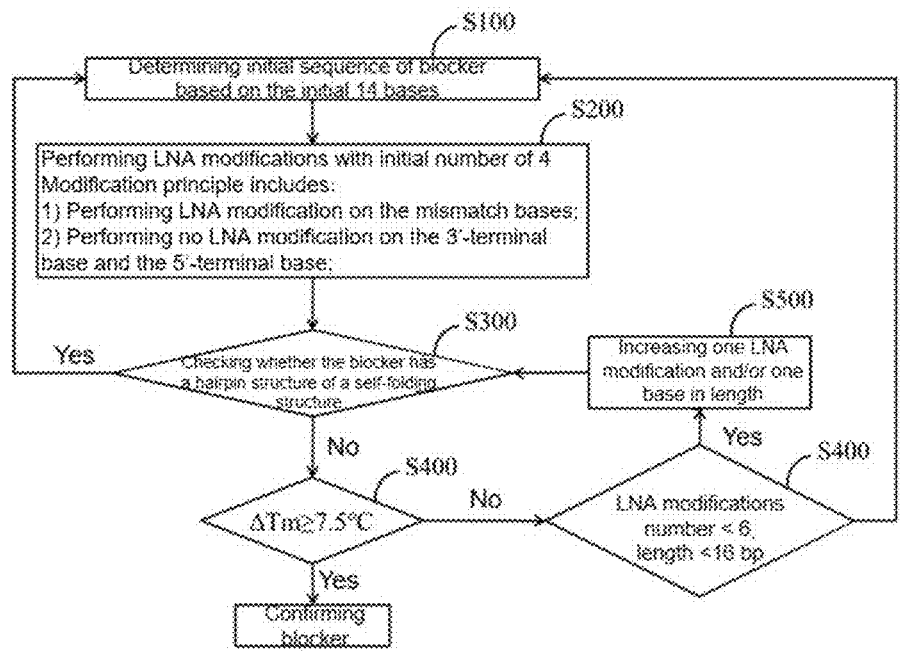
FIG. 9 is a flow chart showing the design process of the blocker in an embodiment of the present invention.
Figure 10A:
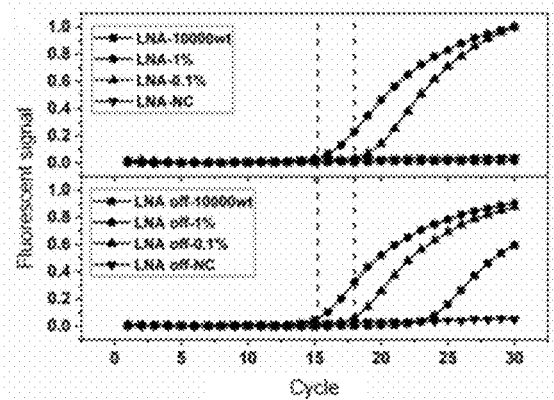
FIG. 10A-FIG. 10C show amplification curves of samples applying different first primers in an embodiment of the present invention.
Figure 10B:
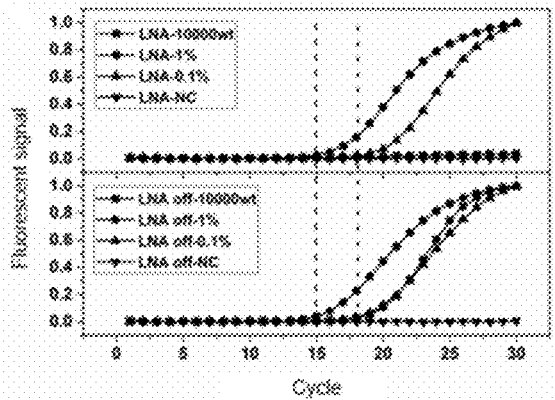
Figure 10C:
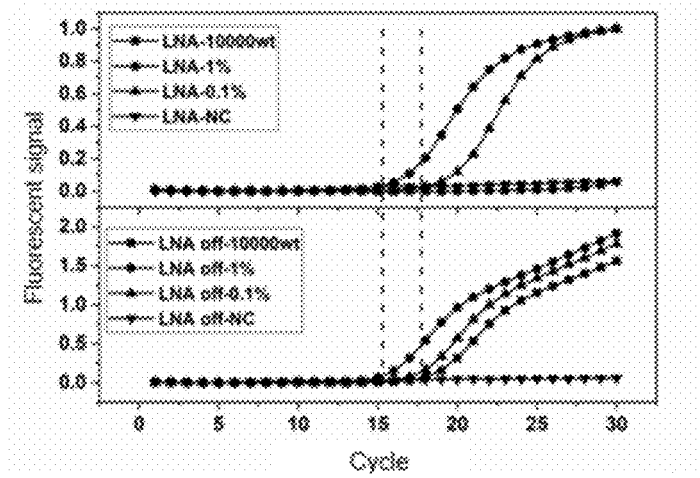

As shown in FIG. 9, the method of designing the blocker was performed by the following steps.

S100, an initial sequence of the blocker was determined based on the initial length of 14 bases.

S200, an LNA modification was performed starting with an initial number of 4 LNA modifications; wherein the LNA modification was performed on a base of the blocker mismatched with the mutant template, and the LNA modification was not performed on the 3'-terminal base nor the 5'-terminal base of the blocker.

S300, whether the blocker had a hairpin structure or a self-folding structure was checked; if not, proceed to S400; and if yes, return to S100.

S400, the melting temperature of the blocker was calculated; and the difference ΔTm obtained from the Tm value of the blocker minus the Tm value of the first primer was checked;

If the difference ΔTm was less than 7.5° C., the number of LNA modifications was less than 6, and the length of the blocker was less than 16 bases, enter S500;

If the difference ΔTm was less than 7.5° C., the number of LNA modifications was 6, and the length of the blocker was equal to 16 bases, enter S100;

If the difference ΔTm was greater than or equal to 7.5° C., it was determined as a suitable blocker.

S500, the number of LNA modifications of the blocker was increased by one, and/or the length of the blocker was increased by one base; then enter S300.

Specifically, in step S400, optionally, ΔTm was controlled within the range of 7.5° C.≤Δ Tm≤12° C.

Optionally, the first primer, the second primer, and the probe needed to be identified, or the first primer must be identified before determining the blocker. The first primer and the second primer were used to specifically amplify the target nucleic acid sequence of the mutant template. The 3'-terminal base of the first primer was complementary to the mutant site of the mutant template, and the Tm of the first primer was greater than or equal to 60° C. When designing the first primer, bases could be added at the 5' end to improve the Tm value if the Tm of the first primer was less than 60° C. Then whether the first primer had a hairpin structure and a self-folding structure was confirmed. If there is, mismatch bases were considered to be introduced to eliminate the hairpin structure and the self-folding structure; if not, the positions and sequences of the second primer and the probe were further determined to check whether there is cross binding; if there is, the position of the primer or the probe was changed; if not, sequences of suitable first primer, second primer and probe were determined.

Embodiment 8 (Verification of Universality of Design Principles for Blockers with Different First Primers)

L861Q was taken as an example for verification. Four different first primers were designed, and Tm values of the four first primers were all greater than or equal to 60° C., as shown in Table 7.

In the verification of this implementation, the second primer used was shown in SEQ ID NO: 8, the TaqMan probe used was shown in SEQ ID NO: 10, and the blocker used was 861 1NA12 (SEQ ID NO: 6, and the calculated Tm value was 74.9° C.).

Table 7 showed that the Tm values of the four different first primers designed were all at least 7.5° C. lower than the Tm value of the blocker.

TABLE 7

Different first primers designed for L861Q site

| Name of first primer | SEQ ID NO: | Sequence (5'-3') | Length | Tm value (° C.) of first primer | ΔTm |
|---|---|---|---|---|---|
| first primer | 9 | TCTTTCTCTTCCGCACCCAGC<u>T</u> | 22 | 66 | 8.9 |
| first primer 2 | 28 | TTTCTCTTCCGCACCCAGC<u>T</u> | 20 | 65.1 | 9.8 |
| first primer 3 | 29 | CTTTCTCTTCCGCACCCAGC<u>T</u> | 21 | 64.7 | 10.2 |
| first primer 4 | 30 | TTCTTTCTCTTCCGCACCCAGC<u>T</u> | 23 | 66.7 | 8.2 |

Note:
Underlines represent the first primers' bases complementary to the mutation sites of mutant template, Result analysis: the amplification curves in FIG. 8A, FIG. 8B, FIG. 8C, FIG. 10A, FIG. 10B and FIG. 10C showed that, for the first primer (SEQ ID NO: 9), the first primer 2 (SEQ ID NO: 28), the first primer 3 (SEQ ID NO: 29) and the first primer 4 (SEQ ID NO: 30), since the differences between the Tm value of the blocker and each of the first primers were all greater than or equal to 7.5° C. (that is, meeting the requirements of the design principles), the blocker could completely inhibit the amplification of wild-type genes after the addition of the blocker 861 LNA12 (FIG. 8C; and upper parts of FIG. 10A, FIG. 10B, and FIG. 10C). Moreover, the blocker almost had no effect on the first primer (SEQ ID NO: 9), the first primer 2 (SEQ ID NO: 28), the first primer 3 (SEQ ID NO: 29) and the first primer 4 (SEQ ID NO: 30) for amplifying the mutant template. The detection sensitivity could reach 0.1%.

The above results indicate that if the design principles of the present embodiment of the invention are used to design blockers, it is not required to use a unique specific first primer. As long as the requirements of the design principles are met, the amplification of wild-type template can be inhibited effectively or completely while not affecting the amplification of the mutant template.

Embodiment 9 (Verification of Generality of Other Single Base Mutation Sites)

According to the method of designing blockers in Embodiment 8, the rapid designs of blockers were carried out for three mutation sites of EGFR S768I, EGFR G719S/G719C, and EGFR T790M, and the effect was checked through experiments, so as to verify the universality of the rapid design method of low-cost blocker in Embodiment 8. The designed blockers are shown in Table 8. The ΔTm values of all blockers are greater than or equal to 7.5° C.

TABLE 8

Blockers designed for different mutation sites

| Blocker name | SEQ ID NO | Sequence (5'-3') | length | Number of LNA modifications | Tm value (° C.) of blocker | Tm 1 | Tm 2 | ΔTm' (° C.) |
|---|---|---|---|---|---|---|---|---|
| 768 LNA | 18 | A*T*GGCCA*G*CG*TGG*AC | 15 | 5 | 79.8 | 79.19 | 67.34 | 11.85 |
| 719 LNA | 19 | CCGGAG*CCC*AGCA*CT* | 15 | 4 | 82.3 | 82.78 | 65.87 | 16.91 |
| 790 LNA | 20 | CT*CATCA*C*G*CAGC*T*CA | 16 | 6 | 78.8 | 81.00 | 69.44 | 11.56 |

Note:
1) Underlines represent the bases corresponding to the mutation sites, and letters in bold italics represent the LNA modification sites.
2) The Tm value of the blocker is obtained by calculation, and the Tm1 and the Tm2 are determined by melting curves.

Figure 11A:
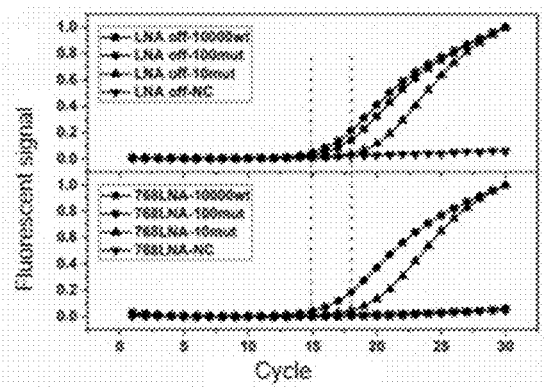
FIG. 11A-FIG. 11C show amplification curves targeted for three epidermal growth factor receptor (EGFR) mutation sites in an embodiment of the present invention.
Figure 11B:
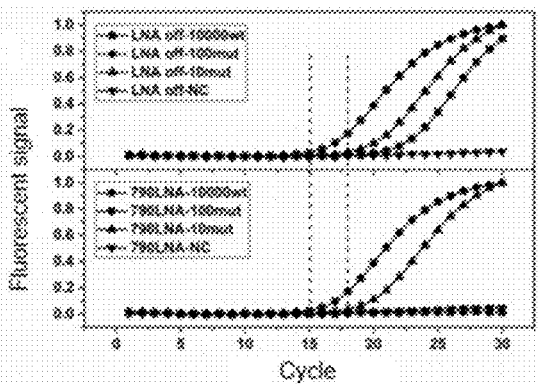
Figure 11C:
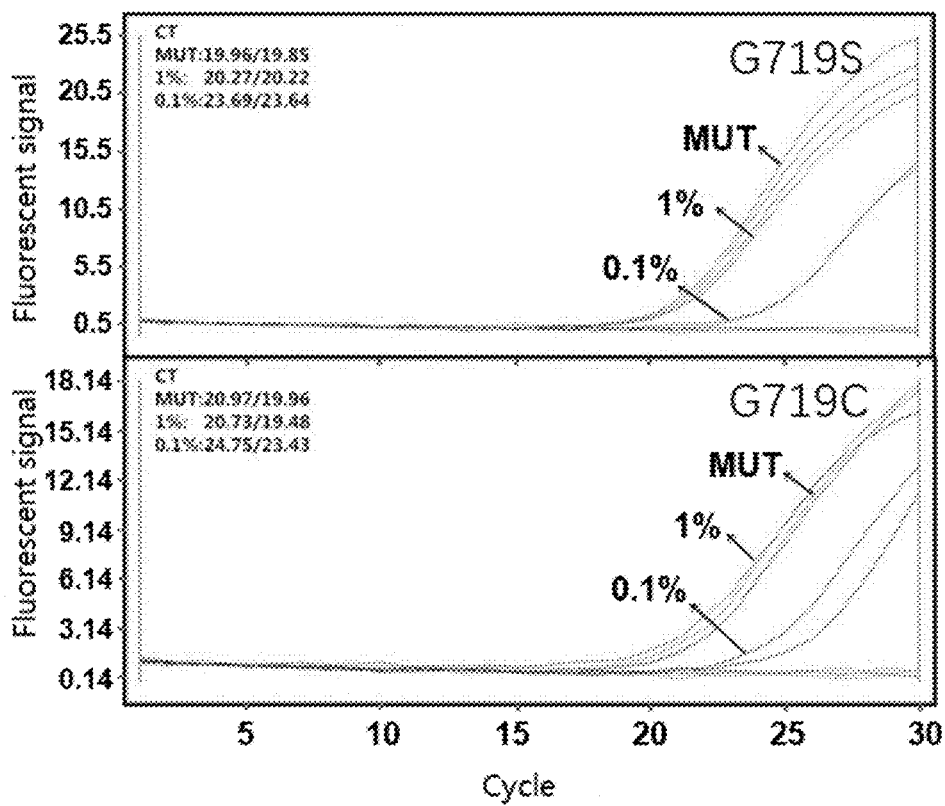

Results Analysis: the amplification curves in FIG. 11A-FIG. 11C showed that, the amplification of wild-type genes could be effectively inhibited by adding blockers at the three sites of EGFR S768I, EGFR T790M and EGFR G719S/G719C (lower parts of FIGS. 11A and 11B; and FIG. 11C). As shown in FIG. 11A and FIG. 11B, the amplification results of 100 copies and 10 copies of pure mutant gene (without wild-type gene in the template) were substantially the same when adding and not adding the blocker, indicating that the aforementioned design principles for blockers are universal and applicable to single-base mutation sites. For the EGFR G719S/G719C mutation site, as shown in FIG. 11C, the wild-type gene could be completely inherited, and the sensitivity could reach 1% or even 0.1%, with a small coefficient of variation (CV). The amplification efficiency of the positive control containing 50 copies of pure mutant gene was basically the same as that of 1% (100 copies of mutant gene+10,000 copies of wild-type gene) mutant template, indicating that the presence of the blocker did not inhibit the PCR reaction.

The foregoing descriptions are merely preferred embodiments of the present invention. It should be understood that one of ordinary skills in the art can make several modifications and variations based on the concept of the present invention without creative efforts. Therefore, any technical solution obtained by a technician in the field based on the prior art through logical analysis, reasoning or limited experiments in accordance with the concept of the present invention shall be within the scope of protection as determined by the claim.

What is claimed is:

1. A composition comprising:
   1) a first primer and a second primer, wherein the first primer and the second primer are used to specifically amplify a target nucleic acid sequence of a first allele variant,
   wherein the 3'-terminal base of the first primer is complementary to a mutation site of the first allele variant, and the Tm value of the first primer is greater than or equal to 60° C.; and
   2) a blocker, wherein a matching region of the blocker is located in an amplification region of the first primer and the second primer, and the 3' end of the blocker is modified with a non-hydroxyl group to inhibit a primer extension reaction, wherein
   the blocker is completely complementary to a second allele variant and has at least one base mismatch with the first allele variant, and the blocker comprises locked nucleic acid (LNA) modifications,
   a difference between a melting temperature (Tm) value of the blocker and a Tm value of the first primer is determined by selecting the number of the LNA modifications, the LNA modification site, and the length of the blocker,
   the blocker comprises a 5' end region, a central region and a 3' end region,
   a base of the blocker mismatched with the first allele variant is located in the central region and is one of the LNA modifications, and the site of mismatch between the blocker and the first allele variation is a mutation site of the first allele variant,
   the 3'-terminal base and the 5'-terminal base of the blocker are not modified with LNA,
   the number of the LNA modifications of the blocker is greater than or equal to 4 and less than or equal to 6,
   the length of the blocker is greater than or equal to 14 bases and less than or equal to 16 bases,
   and the Tm value of the blocker is 7.5° C.-12° C. higher than the Tm value of the first primer.

2. The composition according to claim 1, wherein the first allele variant is a mutant allele, and the second allele variant is a wild-type allele; and the mutation of the first allele variant is a point mutation, an insertion mutation or a deletion mutation.

3. The composition according to claim 1, wherein the nucleotide sequence of the blocker is shown in SEQ ID NO: 6, SEQ ID NO: 7, SEQ ID NO: 18, SEQ ID NO; 19 or SEQ ID NO: 20.

4. The composition according to claim 1, further comprising a detection probe, wherein an amplicon of a mutated target nucleic acid sequence is detected based on a change in detectable properties of the detection probe.

5. A method of designing and synthesizing the blocker in the composition according to claim 1, wherein:
   the blocker is completely complementary to the second allele variant, and the blocker has at east one base mismatch with the first allele variant, the base mismatched with the first allele variant set in the central region of the blocker and one of the LNA modifications; and
   a Tm value of the blocker is designed to be 7.5° C.-12° C. higher than the Tm value of the first primer by adjusting the number of the LNA modifications, the LNA modification sites, and the length of the blocker, the method comprising the following steps:
   adding at east one LNA modification in each adjustment starting with an initial number of 4 LNA modifications, wherein an LNA modification is not added at the 5'-terminal base or the 3'-terminal base of the blocker, and wherein an LNA modification is added at a base of the blocker that is mismatched with the first allele variant, adding at hast one base in length in each adjustment starting with an initial length of 14 bases such that the length of the blocker is greater than or equal to 14 bases and less than or equal to 16 bases, the Tm value of the blocker is 7.5° C.-12° C. higher than the Tm value of the first primer, the number of LNA modifications is greater than or equal to 4 and less than or equal to 6, and the 3' end of the blocker is modified with a non-hydroxyl group to inhibit a primer extension reaction; and synthesizing the blocker.

6. The method of designing and synthesizing the blocker according to claim 5, wherein the following order of steps is performed to design the blocker:
- (S100), determining an initial sequence of the blocker using an initial length of 14 bases;
- (S200), performing the LNA modifications starting with an initial number of 4 LNA modifications; wherein one of the LNA modifications is performed on the base of the blocker mismatched with the first allele variant, and the LNA modifications are not performed on the 3'-terminal base of the blocker or the 5'-terminal base of the blocker;
- (S300), checking whether the blocker has a hairpin structure or a self-folding structure; wherein if the blocker does not have the hairpin structure or the self-folding structure, proceeding to (S400); and wherein if the blocker has the hairpin structure or the self-folding structure, returning to (S100);
- (S400), checking a difference obtained from the Tm value of the blocker minus the Tm value of the first primer;
- wherein if the Tm value of the blocker is less than 7.5° C. higher than the Tm value of the first primer, the number of the LNA modifications is less than 6, and the length of the blocker is less than 16 bases, entering (S500);
- wherein if the Tm value of the blocker is less than 7.5° C. higher than the Tm value of the first primer, the number of the LNA modifications is 6, and the length of the blocker is equal to 16 bases, then returning to (S100); and
- wherein if the Tm value of the blocker is 7.5° C.-12° C. greater than the Tm value of the first primer, the number of LNA modification is between 4 and 6, and the length is between 14 and 16 bases, determining blocker to be a suitable blocker for synthesis; and
- (S500), increasing the number of the LNA modifications of the blocker by one and/or increasing the length of the blocker by one base; and then returning to (S300).

7. A method for detecting allele mutations, comprising:
a) mixing a nucleic acid sample and the composition according to claim 1 to form a reaction mixture;
b) conducting an amplification reaction using the reaction mixture of step a), and forming a target nucleic acid sequence amplicon of the first allele variant using the first primer and the second primer; and
c) performing a detection step;
wherein the reaction mixture of step a) of the method further comprises a detection probe, and step c) of the method is to perform the detection step based on a change in detectable properties of the detection probe to detect the target nucleic acid sequence amplicon of the first allele variant, so as to detect the first allele variant in the nucleic acid sample;
wherein the concentration of the blocker is 5-20 times greater than the concentration of each of the first primer and the second primer.

8. The method according to claim 7, wherein the first allele variant is a mutant allele, and the second allele variant is a wild-type allele; and
the mutation of the first allele variant is a point mutation, an insertion mutation or a deletion mutation.

9. The method according to claim 7, wherein the nucleotide sequence of the blocker is shown in SEQ ID NO: 6, SEQ ID NO: 7, SEQ ID NO: 18, SEQ ID NO: 19 or SEQ ID NO: 20.

10. A kit, comprising: the composition according to claim 1 and further comprising
a detection probe, wherein an amplicon of a mutated target nucleic acid sequence is detected based on a change in detectable properties of the detection probe.

11. The kit according to claim 10, wherein the first allele variant is a mutant allele, and the second allele variant is a wild-type allele; and
the mutation of the first allele variant is a point mutation, an insertion mutation or a deletion mutation.

12. The kit according to claim 10, wherein the nucleotide sequence of the blocker is shown in SEQ ID NO: 6, SEQ ID NO: 7, SEQ ID NO: 18, SEQ ID NO: 19 or SEQ ID NO: 20.

* * * * *

SEQUENCE LISTING

<160> NUMBER OF SEQ ID NOS: 30

<210> SEQ ID NO 1
<211> LENGTH: 21
<212> TYPE: DNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (12)..(12)
<223> OTHER INFORMATION: LNA modified base

<400> SEQUENCE: 1
ccgcacccag cagtttggcc a                                              21

<210> SEQ ID NO 2
<211> LENGTH: 20
<212> TYPE: DNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (11)..(11)
<223> OTHER INFORMATION: LNA modified base

<400> SEQUENCE: 2
cgcacccagc agtttggcca                                                20

<210> SEQ ID NO 3
<211> LENGTH: 19
<212> TYPE: DNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (10)..(11)
<223> OTHER INFORMATION: LNA modified base

<400> SEQUENCE: 3
gcacccagca gtttggcca                                                 19

<210> SEQ ID NO 4
<211> LENGTH: 18
<212> TYPE: DNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (8)..(10)
<223> OTHER INFORMATION: LNA modified bese

<400> SEQUENCE: 4
cacccagcag tttggcca                                                  18

<210> SEQ ID NO 5
<211> LENGTH: 15
<212> TYPE: DNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (6)..(9)
<223> OTHER INFORMATION: LNA modified base

<400> SEQUENCE: 5
acccagcagt ttggc                                              15

<210> SEQ ID NO 6
<211> LENGTH: 15
<212> TYPE: DNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (7)..(8)
<223> OTHER INFORMATION: LNA modified base
<220> FEATURE:
<221> NAME/KEY: misc_feature
<222> LOCATION: (13)..(14)
<223> OTHER INFORMATION: LNA modified base

<400> SEQUENCE: 6
acccagcagt ttggc                                              15

<210> SEQ ID NO 7
<211> LENGTH: 15
<212> TYPE: DNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (2)..(2)
<223> OTHER INFORMATION: LNA modified base
<220> FEATURE:
<221> NAME/KEY: misc_feature
<222> LOCATION: (8)..(8)
<223> OTHER INFORMATION: LNA modified base
<220> FEATURE:
<221> NAME/KEY: misc_feature
<222> LOCATION: (12)..(13)
<223> OTHER INFORMATION: LNA modified base

<400> SEQUENCE: 7
acccagcagt ttggc                                              15

<210> SEQ ID NO 8
<211> LENGTH: 19
<212> TYPE: DNA
<213> ORGANISM: Artificial Sequence
<220> FEATURE:
<223> OTHER INFORMATION: The sequence is synthesized

<400> SEQUENCE: 8
cttggtgcac cgcgacctg                                          19

<210> SEQ ID NO 9
<211> LENGTH: 22
<212> TYPE: DNA
<213> ORGANISM: Artificial Sequence
<220> FEATURE:
<223> OTHER INFORMATION: The sequence is synthesized

<400> SEQUENCE: 9
tctttctctt ccgcacccag ct                                      22

<210> SEQ ID NO 10
<211> LENGTH: 16
<212> TYPE: DNA
<213> ORGANISM: Artificial Sequence
<220> FEATURE:
<223> OTHER INFORMATION: The sequence is synthesized

```
<400> SEQUENCE: 10
cacgtgtgcc gcctgc                                                  16

<210> SEQ ID NO 11
<211> LENGTH: 11
<212> TYPE: DNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (1)..(1)
<223> OTHER INFORMATION: LNA modified base
<220> FEATURE:
<221> NAME/KEY: misc_feature
<222> LOCATION: (3)..(3)
<223> OTHER INFORMATION: LNA modified base
<220> FEATURE:
<221> NAME/KEY: misc_feature
<222> LOCATION: (5)..(5)
<223> OTHER INFORMATION: LNA modified base
<220> FEATURE:
<221> NAME/KEY: misc_feature
<222> LOCATION: (7)..(7)
<223> OTHER INFORMATION: LNA modified base
<220> FEATURE:
<221> NAME/KEY: misc_feature
<222> LOCATION: (9)..(9)
<223> OTHER INFORMATION: LNA modified base
<220> FEATURE:
<221> NAME/KEY: misc_feature
<222> LOCATION: (11)..(11)
<223> OTHER INFORMATION: LNA modified base

<400> SEQUENCE: 11
cagcagtttg g                                                       11

<210> SEQ ID NO 12
<211> LENGTH: 12
<212> TYPE: DNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (2)..(2)
<223> OTHER INFORMATION: LNA modified base
<220> FEATURE:
<221> NAME/KEY: misc_feature
<222> LOCATION: (4)..(4)
<223> OTHER INFORMATION: LNA modified base
<220> FEATURE:
<221> NAME/KEY: misc_feature
<222> LOCATION: (6)..(6)
<223> OTHER INFORMATION: LNA modified base
<220> FEATURE:
<221> NAME/KEY: misc_feature
<222> LOCATION: (8)..(8)
<223> OTHER INFORMATION: LNA modified base
<220> FEATURE:
<221> NAME/KEY: misc_feature
<222> LOCATION: (10)..(10)
<223> OTHER INFORMATION: LNA modified base
<220> FEATURE:
<221> NAME/KEY: misc_feature
<222> LOCATION: (12)..(12)
<223> OTHER INFORMATION: LNA modified base

<400> SEQUENCE: 12
ccagcagttt gg                                                      12

<210> SEQ ID NO 13
<211> LENGTH: 13
```

```
<212> TYPE: DNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (1)..(1)
<223> OTHER INFORMATION: LNA modified base
<220> FEATURE:
<221> NAME/KEY: misc_feature
<222> LOCATION: (3)..(3)
<223> OTHER INFORMATION: LNA modified base
<220> FEATURE:
<221> NAME/KEY: misc_feature
<222> LOCATION: (5)..(5)
<223> OTHER INFORMATION: LNA modified base
<220> FEATURE:
<221> NAME/KEY: misc_feature
<222> LOCATION: (7)..(7)
<223> OTHER INFORMATION: LNA modified base
<220> FEATURE:
<221> NAME/KEY: misc_feature
<222> LOCATION: (9)..(9)
<223> OTHER INFORMATION: LNA modified base
<220> FEATURE:
<221> NAME/KEY: misc_feature
<222> LOCATION: (11)..(11)
<223> OTHER INFORMATION: LNA modified base
<220> FEATURE:
<221> NAME/KEY: misc_feature
<222> LOCATION: (13)..(13)
<223> OTHER INFORMATION: LNA modified base

<400> SEQUENCE: 13
cccagcagtt tgg                                                          13

<210> SEQ ID NO 14
<211> LENGTH: 14
<212> TYPE: DNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (2)..(2)
<223> OTHER INFORMATION: LNA modified base
<220> FEATURE:
<221> NAME/KEY: misc_feature
<222> LOCATION: (4)..(4)
<223> OTHER INFORMATION: LNA modified base
<220> FEATURE:
<221> NAME/KEY: misc_feature
<222> LOCATION: (6)..(6)
<223> OTHER INFORMATION: LNA modified base
<220> FEATURE:
<221> NAME/KEY: misc_feature
<222> LOCATION: (8)..(8)
<223> OTHER INFORMATION: LNA modified base
<220> FEATURE:
<221> NAME/KEY: misc_feature
<222> LOCATION: (10)..(10)
<223> OTHER INFORMATION: LNA modified base
<220> FEATURE:
<221> NAME/KEY: misc_feature
<222> LOCATION: (12)..(12)
<223> OTHER INFORMATION: LNA modified base
<220> FEATURE:
<221> NAME/KEY: misc_feature
<222> LOCATION: (14)..(14)
<223> OTHER INFORMATION: LNA modified base

<400> SEQUENCE: 14
acccagcagt ttgg                                                         14

<210> SEQ ID NO 15
```

```
<211> LENGTH: 15
<212> TYPE: DNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (1)..(1)
<223> OTHER INFORMATION: LNA modified base
<220> FEATURE:
<221> NAME/KEY: misc_feature
<222> LOCATION: (3)..(3)
<223> OTHER INFORMATION: LNA modified base
<220> FEATURE:
<221> NAME/KEY: misc_feature
<222> LOCATION: (5)..(5)
<223> OTHER INFORMATION: LNA modified base
<220> FEATURE:
<221> NAME/KEY: misc_feature
<222> LOCATION: (7)..(7)
<223> OTHER INFORMATION: LNA modified base
<220> FEATURE:
<221> NAME/KEY: misc_feature
<222> LOCATION: (9)..(9)
<223> OTHER INFORMATION: LNA modified base
<220> FEATURE:
<221> NAME/KEY: misc_feature
<222> LOCATION: (11)..(11)
<223> OTHER INFORMATION: LNA modified base
<220> FEATURE:
<221> NAME/KEY: misc_feature
<222> LOCATION: (13)..(13)
<223> OTHER INFORMATION: LNA modified base
<220> FEATURE:
<221> NAME/KEY: misc_feature
<222> LOCATION: (15)..(15)
<223> OTHER INFORMATION: LNA modified base

<400> SEQUENCE: 15
cacccagcag tttgg                                                         15

<210> SEQ ID NO 16
<211> LENGTH: 21
<212> TYPE: DNA
<213> ORGANISM: Artificial Sequence
<220> FEATURE:
<223> OTHER INFORMATION: The sequence is synthesized

<400> SEQUENCE: 16
ccgcacccag cagtttggcc a                                                  21

<210> SEQ ID NO 17
<211> LENGTH: 15
<212> TYPE: DNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (1)..(1)
<223> OTHER INFORMATION: LNA modified base
<220> FEATURE:
<221> NAME/KEY: misc_feature
<222> LOCATION: (3)..(3)
<223> OTHER INFORMATION: LNA modified base
<220> FEATURE:
<221> NAME/KEY: misc_feature
<222> LOCATION: (5)..(5)
<223> OTHER INFORMATION: LNA modified base
<220> FEATURE:
<221> NAME/KEY: misc_feature
<222> LOCATION: (7)..(7)
<223> OTHER INFORMATION: LNA modified base
<220> FEATURE:
<221> NAME/KEY: misc_feature
```

```
<222> LOCATION: (11)..(11)
<223> OTHER INFORMATION: LNA modified base
<220> FEATURE:
<221> NAME/KEY: misc_feature
<222> LOCATION: (13)..(13)
<223> OTHER INFORMATION: LNA modified base
<220> FEATURE:
<221> NAME/KEY: misc_feature
<222> LOCATION: (15)..(15)
<223> OTHER INFORMATION: LNA modified base

<400> SEQUENCE: 17
cacccagcag tttgg                                               15

<210> SEQ ID NO 18
<211> LENGTH: 15
<212> TYPE: DNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (2)..(2)
<223> OTHER INFORMATION: LNA modified base
<220> FEATURE:
<221> NAME/KEY: misc_feature
<222> LOCATION: (8)..(8)
<223> OTHER INFORMATION: LNA modified base
<220> FEATURE:
<221> NAME/KEY: misc_feature
<222> LOCATION: (11)..(13)
<223> OTHER INFORMATION: LNA modified base

<400> SEQUENCE: 18
atggccagcg tggac                                               15

<210> SEQ ID NO 19
<211> LENGTH: 15
<212> TYPE: DNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (7)..(9)
<223> OTHER INFORMATION: LNA modified base
<220> FEATURE:
<221> NAME/KEY: misc_feature
<222> LOCATION: (14)..(14)
<223> OTHER INFORMATION: LNA modified base

<400> SEQUENCE: 19
ccggagccca gcact                                               15

<210> SEQ ID NO 20
<211> LENGTH: 16
<212> TYPE: DNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (3)..(3)
<223> OTHER INFORMATION: LNA modified base
<220> FEATURE:
<221> NAME/KEY: misc_feature
<222> LOCATION: (6)..(6)
<223> OTHER INFORMATION: LNA modified base
<220> FEATURE:
<221> NAME/KEY: misc_feature
<222> LOCATION: (8)..(9)
<223> OTHER INFORMATION: LNA modified base
<220> FEATURE:
```

```
<221> NAME/KEY: misc_feature
<222> LOCATION: (13)..(13)
<223> OTHER INFORMATION: LNA modified base
<220> FEATURE:
<221> NAME/KEY: misc_feature
<222> LOCATION: (15)..(15)
<223> OTHER INFORMATION: LNA modified base

<400> SEQUENCE: 20
ctcatcacgc agctca                                                           16

<210> SEQ ID NO 21
<211> LENGTH: 21
<212> TYPE: DNA
<213> ORGANISM: Artificial Sequence
<220> FEATURE:
<223> OTHER INFORMATION: The sequence is synthesized

<400> SEQUENCE: 21
tggccaaact gctgggtgcg g                                                     21

<210> SEQ ID NO 22
<211> LENGTH: 21
<212> TYPE: DNA
<213> ORGANISM: Artificial Sequence
<220> FEATURE:
<223> OTHER INFORMATION: The sequence is synthesized

<400> SEQUENCE: 22
tggccaaaca gctgggtgcg g                                                     21

<210> SEQ ID NO 23
<211> LENGTH: 400
<212> TYPE: DNA
<213> ORGANISM: Artificial Sequence
<220> FEATURE:
<223> OTHER INFORMATION: The sequence is synthesized

<400> SEQUENCE: 23
agcctggcat gaacatgacc ctgaattcgg atgcagagct tcttcccatg atgatctgtc           60
cctcacagca gggtcttctc tgtttcaggg catgaactac ttggaggacc gtcgcttggt          120
gcaccgcgac ctggcagcca ggaacgtact ggtgaaaaca ccgcagcatg tcaagatcac          180
agattttggg ctggccaaac agctgggtgc ggaagagaaa gaataccatg cagaaggagg          240
caaagtaagg aggtggcttt aggtcagcca gcattttcct gacaccaggg accaggctgc          300
cttcccacta gctgtattgt ttaacacatg caggggagga tgctctccag acattctggg          360
tgagctcgca gcagctgctg ctggcagctg ggtccagcca                                400

<210> SEQ ID NO 24
<211> LENGTH: 400
<212> TYPE: DNA
<213> ORGANISM: Artificial Sequence
<220> FEATURE:
<223> OTHER INFORMATION: The sequence is synthesized

<400> SEQUENCE: 24
tacgtatttt gaaactcaag atcgcattca tgcgtcttca cctggaaggg gtccatgtgc           60
ccctccttct ggccaccatg cgaagccaca ctgacgtgcc tctccctccc tccaggaagc          120
ctacgtgatg gccagcgtgg acaacccccca cgtgtgccgc ctgctgggca tctgcctcac         180
ctccaccgtg cagctcatca tgcagctcat gcccttcggc tgcctcctgg actatgtccg          240
ggaacacaaa gacaatattg ctcccagta cctgctcaac tggtgtgtgc agatcgcaaa          300
```
ggtaatcagg gaagggagat acggggaggg gagataagga gccaggatcc tcacatgcgg    360
tctgcgctcc tgggatagca agagtttgcc atgggatat                          400

<210> SEQ ID NO 25
<211> LENGTH: 400
<212> TYPE: DNA
<213> ORGANISM: Artificial Sequence
<220> FEATURE:
<223> OTHER INFORMATION: The sequence is synthesized

<400> SEQUENCE: 25
acttcacagc cctgcgtaaa cgtccctgtg ctaggtcttt tgcaggcaca gcttttcctc     60
catgagtacg tattttgaaa ctcaagatcg cattcatgcg tcttcacctg gaagggtcc    120 atgtgcccct ccttctggcc accatgcgaa gccacactga cgtgcctctc cctccctcca   180
ggaagcctac gtgatggcca tcgtggacaa ccccacgtg tgccgcctgc tgggcatctg    240
cctcacctcc accgtgcagc tcatcacgca gctcatgccc ttcggctgcc tcctggacta   300
tgtccgggaa cacaaagaca atattggctc ccagtacctg ctcaactggt gtgtgcagat   360
cgcaaaggta atcagggaag ggagatacgg ggaggggaga                          400

<210> SEQ ID NO 26
<211> LENGTH: 400
<212> TYPE: DNA
<213> ORGANISM: Artificial Sequence
<220> FEATURE:
<223> OTHER INFORMATION: The sequence is synthesized

<400> SEQUENCE: 26
agcccatgcc gtggctgctg gtcccccctgc tgggccatgt ctggcactgc tttccagcat    60
ggtgagggct gaggtgaccc ttgtctctgt gttcttgtcc cccccagctt gtggagcctc   120
ttacacccag tggagaagct cccaaccaag ctctcttgag gatcttgaag gaaactgaat   180
tcaaaaagat caaagtgctg agctccggtg cgttcggcac ggtgtataag gtaaggtccc   240
tggcacaggc ctctgggctg gccgcaggg cctctcatgg tctggtgggg agcccagagt    300
ccttgcaagc tgtatatttc catcatctac tttactcttt gtttcactga gtgtttggga   360
aactccagtg ttttttcccaa gttattgaga ggaaatcttt                         400

<210> SEQ ID NO 27
<211> LENGTH: 400
<212> TYPE: DNA
<213> ORGANISM: Artificial Sequence
<220> FEATURE:
<223> OTHER INFORMATION: The sequence is synthesized

<400> SEQUENCE: 27
agcccatgcc gtggctgctg gtcccccctgc tgggccatgt ctggcactgc tttccagcat    60
ggtgagggct gaggtgaccc ttgtctctgt gttcttgtcc cccccagctt gtggagcctc   120
ttacacccag tggagaagct cccaaccaag ctctcttgag gatcttgaag gaaactgaat   180
tcaaaaagat caaagtgctg tgctccggtg cgttcggcac ggtgtataag gtaaggtccc   240
tggcacaggc ctctgggctg gccgcaggg cctctcatgg tctggtgggg agcccagagt    300
ccttgcaagc tgtatatttc catcatctac tttactcttt gtttcactga gtgtttggga   360
aactccagtg ttttttcccaa gttattgaga ggaaatcttt                         400

<210> SEQ ID NO 28

```
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 28
tttctcttcc gcacccagct                                               20

<210> SEQ ID NO 29
<211> LENGTH: 21
<212> TYPE: DNA
<213> ORGANISM: Artificial Sequence
<220> FEATURE:
<223> OTHER INFORMATION: The sequence is synthesized

<400> SEQUENCE: 29
ctttctcttc cgcacccagc t                                             21

<210> SEQ ID NO 30
<211> LENGTH: 23
<212> TYPE: DNA
<213> ORGANISM: Artificial Sequence
<220> FEATURE:
<223> OTHER INFORMATION: The sequence is synthesized

<400> SEQUENCE: 30
ttctttctct tccgcaccca gct                                           23
```